(12) United States Patent
Angelico

(10) Patent No.: US 11,554,230 B2
(45) Date of Patent: Jan. 17, 2023

(54) VENTILATOR-INITIATED DECISION SUPPORT AND WAVEFORM CAPTURE DURING VENTILATION

(71) Applicant: Covidien LP, Mansfield, MA (US)

(72) Inventor: Phyllis Rae Angelico, San Marcos, CA (US)

(73) Assignee: Covidien LP, Mansfield, MA (US)

( * ) Notice: Subject to any disclaimer, the term of this patent is extended or adjusted under 35 U.S.C. 154(b) by 438 days.

(21) Appl. No.: 16/743,252

(22) Filed: Jan. 15, 2020

(65) Prior Publication Data

US 2020/0230336 A1 Jul. 23, 2020

Related U.S. Application Data

(60) Provisional application No. 62/793,639, filed on Jan. 17, 2019.

(51) Int. Cl.
*A61M 16/00* (2006.01)
*G16H 40/60* (2018.01)
(Continued)

(52) U.S. Cl.
CPC .... *A61M 16/0051* (2013.01); *A61M 16/0057* (2013.01); *A61M 16/024* (2017.08);
(Continued)

(58) Field of Classification Search
CPC .............. A61M 16/00; A61M 16/0051; A61M 16/0057; A61M 16/0069; A61M 16/022;
(Continued)

(56) References Cited

U.S. PATENT DOCUMENTS

| | | | |
|---|---|---|---|
| 2011/0138323 A1* | 6/2011 | Skidmore | A61M 16/0051 715/846 |
| 2012/0204875 A1* | 8/2012 | Brazy | A61M 16/0051 128/204.22 |

(Continued)

FOREIGN PATENT DOCUMENTS

| | | |
|---|---|---|
| CN | 103169476 B | 3/2015 |
| EP | 2465434 A1 | 6/2012 |

(Continued)

OTHER PUBLICATIONS

PCT International Search Report and Written Opinion in International Application PCT/US2020/013763, dated Apr. 14, 2020, 17 pages.

(Continued)

*Primary Examiner* — Joseph D. Boecker

(57) ABSTRACT

Systems and methods for clinician decision support during mechanical ventilation of a patient comprise evaluating a shape and/or characteristics of a waveform to detect an anomaly. While mechanical ventilators are equipped with a number of alarms and alerts when monitored patient data breaches various alarm thresholds, some anomalies in patient data may go unnoticed by clinicians. These anomalies, however, may provide relevant information regarding patient condition. Accordingly, in response to detecting an anomaly, the ventilator captures at least a portion of the waveform. The waveform capture, which may be annotated with various labels and educational information, may be reviewed by a clinician to obtain additional information regarding the anomaly. In this way, clinicians may be trained to recognize and address anomalies associated with waveform data and thereby be armed with information to optimize patient-ventilator interaction.

20 Claims, 11 Drawing Sheets

(51) Int. Cl.
  *G16H 50/20* (2018.01)
  *G06T 11/60* (2006.01)
  *G06F 3/04842* (2022.01)

(52) U.S. Cl.
  CPC .......... *G06F 3/04842* (2013.01); *G06T 11/60* (2013.01); *G16H 40/60* (2018.01); *G16H 50/20* (2018.01); *A61M 2016/003* (2013.01); *A61M 2016/0027* (2013.01); *A61M 2205/502* (2013.01); *A61M 2205/584* (2013.01); *G06T 2210/41* (2013.01)

(58) Field of Classification Search
  CPC .......... A61M 16/024; A61M 2205/502; A61M 2205/505; A61M 2205/52; A61M 2016/0027; A61M 2016/003; A61M 2016/0033; A61B 5/742; A61B 5/743; A61B 5/7445; G16H 40/60; G16H 50/20; G06F 3/04842
  See application file for complete search history.

(56) References Cited

U.S. PATENT DOCUMENTS

| | | | |
|---|---|---|---|
| 2013/0032149 A1* | 2/2013 | Robinson | G16H 40/63 128/204.21 |
| 2016/0206837 A1 | 7/2016 | Dong et al. | |
| 2017/0367618 A1 | 12/2017 | Ricciardelli et al. | |

FOREIGN PATENT DOCUMENTS

| WO | 2012/148356 A1 | 11/2012 |
|---|---|---|
| WO | 2017/095241 A2 | 6/2017 |

OTHER PUBLICATIONS

Duke Health, 15th Optimizing Mechanical Ventilation for Infants and Children Conference: Talk on Airway Graphic Analysis: A Bedside Tool, by Ira Cheifetz, MD, Apr. 16-18, 2018, 5 pages.

De Wit, Marjolein, "Monitoring of Patient-Ventilator Interaction at the Bedside", Respiratory Care, Jan. 2011, vol. 56, No. 1, pp. 61-72.

Walsh, Brian K. et al., "Electrical Impedance Tomography During Medical Ventilation", https://doi.org/10.4187/respcare.04914, Respiratory Care, Oct. 2016, 61 (10); 1417-1424.

Epstein, Scott K, "How often does patient-ventilator asynchrony occur and what are the consequences?", Respiratory Care, Jan. 2011; vol. 56: 25-38.

Ramirez II, Arellano DH, Adasme RS, Landeros JM, Salinas FA, Vargas AG, et al. Ability of ICU health-care professionals to identify patient-ventilator asynchrony using waveform analysis. Respir Care 2017;62(2):144-149.

Tobin MJ, Jubran A, Laghi F. Patient-ventilator interaction. American Journal Of Respiratory And Critical Care Medicine. 2001;163(5):1059-63. PubMed PMID: 11316635.

Colombo et al: Efficacy of ventilator waveforms observation in detecting patient-ventilator asynchrony. Crit Care Med 2011 vol. 39, No. 11, 6 pages.

Hess, Dean. Ventialtor Waveforms and the Physiology of Pressure Support Ventilation, Respiratory Care • Feb. 2005, vol. 50, No. 2, pp. 166-186.

* cited by examiner

VENTILATOR-INITIATED DECISION SUPPORT AND WAVEFORM CAPTURE DURING VENTILATION

RELATED APPLICATIONS

This application claims the benefit of U.S. Provisional Application No. 62/793,639, filed on Jan. 17, 2019, which is hereby incorporated by reference in its entirety.

BACKGROUND

Medical ventilator systems have long been used to provide ventilatory and supplemental oxygen support to patients. These ventilators typically comprise a connection for pressurized gas (air, oxygen) that is delivered to the patient through a conduit or tubing. As each patient may require a different ventilation strategy, modern ventilators can be customized for the particular needs of an individual patient. For example, several different ventilator modes or settings have been created to provide better ventilation for patients in different scenarios, such as mandatory ventilation modes, spontaneous ventilation modes, and assist-control ventilation modes. Ventilators monitor a variety of patient parameters and are well equipped to provide reports and other information regarding a patient's condition. Unfortunately, clinicians are often unable to interpret the ventilator information in order to make educated assessments of the patient.

It is with respect to this general technical environment that aspects of the present technology disclosed herein have been contemplated. Furthermore, although a general environment has been discussed, it should be understood that the examples described herein should not be limited to the general environment identified herein.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

Aspects of the disclosure relate to providing systems and methods for clinician decision support during mechanical ventilation of a patient. More specifically, this disclosure describes systems and methods for ventilation-initiated decision support during ventilation via waveform capture when a clinical anomaly is detected. An anomaly is defined as an irregularity in monitored patient data that may not be sufficient to trigger an alarm. The anomaly may be detected and a screenshot of the corresponding waveform may be captured automatically, enabling clinicians to remain abreast of a patient's condition even when treating other patients. The screenshot capture, as well as educational materials regarding the anomaly, may be viewed at any time, enabling clinicians to research an anomaly at their convenience.

Among other things, aspects of the present disclosure include systems and methods for ventilator-implemented decision support based on waveform captures. In aspects, a ventilator including a processor and memory storing computer executable instructions that when executed by the processor cause the ventilator to perform steps. The computer executable instructions causing the ventilator to collect data from one or more sensors monitoring one or more parameters during ventilation of a patient and, as the data is collected, graphically represent the data as a waveform in a first window of a display operatively coupled to the ventilator. The ventilator further monitoring at least one of a shape or a characteristic of the waveform and detecting an anomaly based on at least one of the shape or the characteristic. Further, in response to detecting the anomaly, the ventilator automatically captures a screenshot of the waveform including the anomaly and displays an anomaly detection icon in the first window. In response to a selection of the anomaly detection icon, the ventilator provides a second window displaying the captured screenshot.

In further aspects, a ventilator-implemented method for providing decision support during ventilation of a patient is provided. The method including collecting data from one or more sensors monitoring one or more parameters during ventilation of the patient by a ventilator and, as the data is collected, graphically representing the data as a waveform in a first window of a display operatively coupled to the ventilator. The method further including monitoring at least one of a shape or a characteristic of the waveform and detecting an anomaly based on at least one of the shape or the characteristic. In response to detecting the anomaly, the method including capturing a portion of the waveform including the anomaly and providing a second window displaying the captured portion of the waveform.

In still further aspects, another ventilator-implemented method for providing decision support during ventilation is provided. The method including collecting data from one or more sensors monitoring one or more parameters during ventilation of a patient by a ventilator and, as the data is collected, graphically representing the data as a waveform in a first window of a display operatively coupled to the ventilator. The method further including monitoring at least one of a shape or a characteristic of the waveform and detecting an anomaly based on at least one of the shape or the characteristic. In response to detecting the anomaly, the method also including capturing a portion of the waveform including the anomaly and displaying an anomaly detection icon in the first window.

It is to be understood that both the foregoing general description and the following Detailed Description are exemplary and explanatory and are intended to provide further explanation of the disclosure as claimed.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

Figure 1:
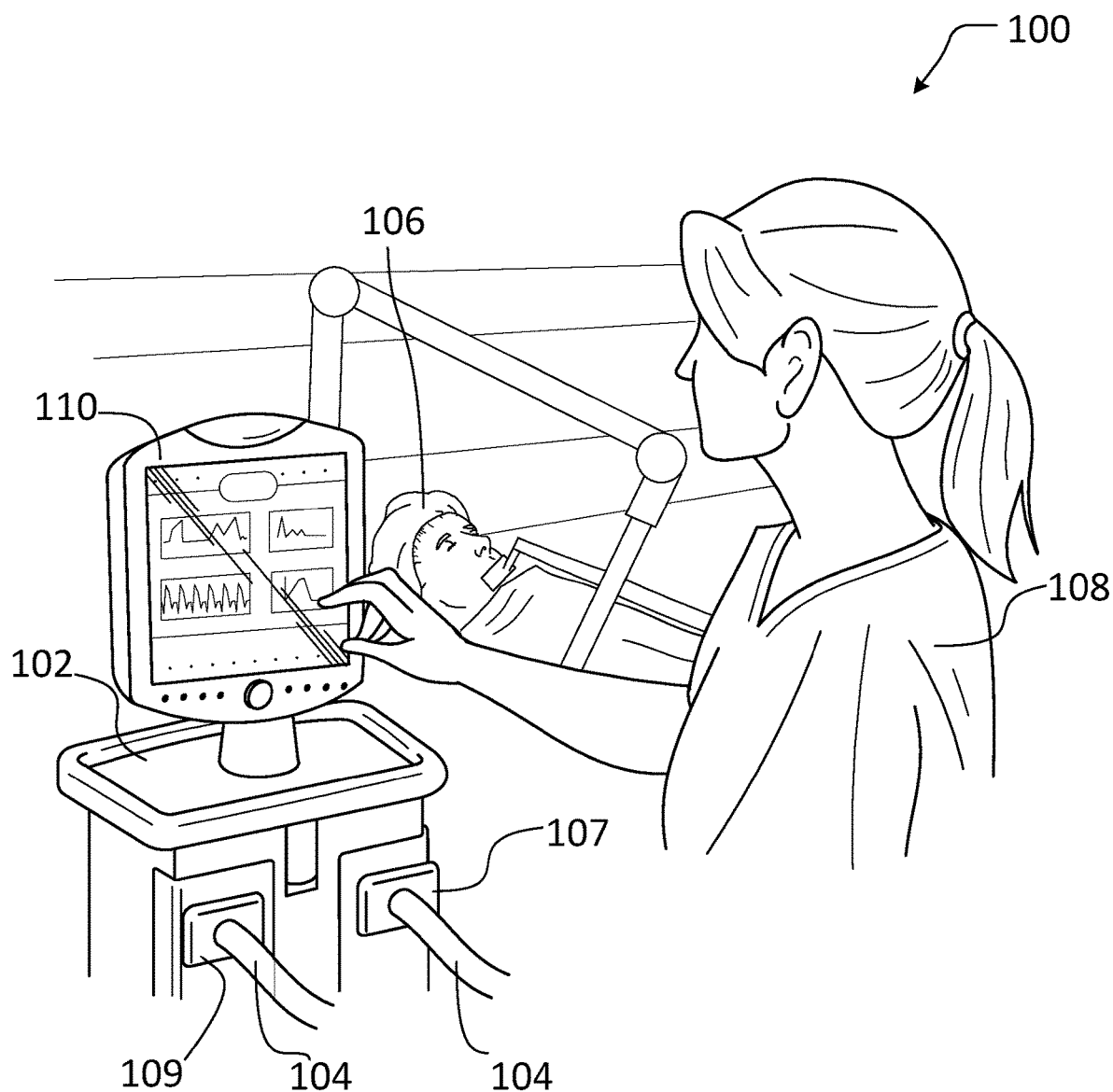
FIG. 1 is a schematic diagram illustrating a ventilator capable of providing clinician decision support during mechanical ventilation of a patient, in accordance with aspects of the disclosure.

While embodiments of the disclosure are amenable to various modifications and alternative forms, specific embodiments have been shown by way of example in the drawings and are described in detail below. The intention is not to limit the scope of the disclosure to the particular embodiments described. On the contrary, the disclosure is intended to cover all modifications, equivalents, and alternatives falling within the scope of the disclosure and the appended claims.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients, general gas transport systems, or other monitors including an electrocardiogram (EKG) monitor, a capnography monitor ($CO_2$), a pulse oximeter ($SpO_2$), Electroencephalography (EEG) monitor, and the like.

As described herein, real-time display may mean a variety of things, including but not limited to contemporaneous display, or any other display of data at the time of collection or calculation, to be analyzed along with the current ventilation status of a patient from whom measurements are being collected.

Medical ventilators are used to provide breathing gases to patients who are otherwise unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gases having a desired concentration are supplied to the patient at desired pressures and flow rates. Modern ventilators monitor, evaluate, and graphically represent a myriad of ventilatory parameters. However, many clinicians may not easily identify or recognize data patterns (e.g., within patient waveforms) and correlations indicative of certain patient conditions or changes in patient condition.

Waveform analysis by visual inspection can be a reliable, noninvasive, and useful tool for detecting patient-ventilator asynchrony. However, waveform analysis is a skill that requires a properly trained professional. For example, an observational study conducted in seventeen urban intensive care units (ICUs) evaluated a total of 366 health care providers (HCPs) (with and without prior mechanical ventilation training) for their ability to recognize different types of asynchrony. Only seventy-eight of the HCPs (21.3%) recognized the three presented types of asynchrony correctly, whereas 111 (30.3%) detected two types correctly, and 116 (31.7%) detected one type correctly. Sixty-one participants (16.7%) did not identify any asynchrony. See Ramirez II et al., "Ability of ICU health-care professionals to identify patient-ventilator asynchrony using waveform analysis," Respir. Care 2017; 62(2):144-149.

Mechanical ventilators are equipped with a number of alarms and alerts when monitored patient data breaches various alarm thresholds, but some anomalies in patient data may go unnoticed by clinicians. These anomalies, however, may provide relevant information regarding patient condition. For example, clinicians may not be generally proficient at recognizing clinically significant graphic changes and responding in a timely manner to those changes such that patient clinical harm can be prevented. Academic centers in the developed countries have mechanical ventilation subject-matter experts ("SMEs"), who may do research and/or who may teach, report on, understand, and use graphics extensively. However, many caregivers in the ICU are not privy to such research or learning and do not have the proper training or confidence to make decisions on the graphic information presented. At a pediatric/neonatal conference on mechanical ventilation attended by physicians and respiratory therapists, an SME presented a review of ventilator graphic waveforms. When the SME queried the audience for who understood and used waveforms to gain clinical information, very few participants responded affirmatively.

Additionally, even if ventilators calculate and present real-time waveforms associated with a patient condition over a period of time, some important data may be missed if the patient is left unattended for even a minimal period.

As such, systems and methods disclosed herein provide a decision support tool that addresses these problems by capturing and storing anomalous events, along with educational materials regarding the events, so that instant training information is available at a clinician's fingertips. Failure to recognize and respond to the valuable information that graphic waveforms offer is a disservice to the patient and may prolong his or her course of mechanical ventilation or impact the acuity of the patient's condition.

With these broad concepts in mind, several examples of ventilation-initiated decision support via waveform capture during ventilation are discussed, below.

For example, FIG. 1 shows a schematic diagram 100 that illustrates a ventilator 102 capable of providing decision support during ventilation. As shown, the schematic diagram 100 comprises a ventilator 102, a patient circuit 104, patient 106, clinician 108, and display 110. The ventilator 102 may engage one or more data collection sensors (not shown) to monitor various parameters that may be measured or calculated based on the closed system between the ventilator 102 and the patient 106. For example, the data collection sensors may collect one or more of gas flow, pressure, volume, or any other measurement that may be measured, calculated, or derived based on ventilation of the patient 106, measured at either or both the inhalation port 107 and exhalation port 109 of the ventilator. In an embodiment, the ventilator 102 includes pressure and flow sensors at the inhalation port 107 that measure pressure and flow of the inhalation gases flowing into the patient circuit 104, and pressure and flow sensors at the exhalation port 109 that measure pressure and flow of the exhalation gases returning to the ventilator from the patient. The ventilator 102 may also receive pressure and flow measurements from sensors along the patient circuit 104, but these are optional, as discussed further below. This measured, collected, or calculated data may be used by the clinician 108 or ventilator 102 when determining potential adjustments or changes to settings of the ventilator 102 in order to optimize patient-ventilator interaction. While collecting data, the ventilator 102 may analyze and/or graph the data, as a function of time or another parameter (e.g., volume), to determine one or more waveforms. These waveforms may be used by the clinician 108 in determining potential adjustments or changes to settings of the ventilator 102 in order to optimize treatment.

The waveforms (which may include any variety of parameters such as flow, pressure, volume, and the like, as a function of time or another parameter) may be shown on a display 110 of the ventilator 102. As an example, the display 110 may provide waveforms representative of data collected up to and including the current time. As a further example, the display 110 may show a time period that is the equivalent of multiple breaths of the patient 106. This time period may be lengthened or shortened to show more or less breaths. For example, the display 110 may show a waveform that represents data as a function of time for the last two or three breaths of the patient 106. This waveform may be updated on the display 110 in real time, or substantially real time, as the data is collected and/or calculated. Thus, the waveform on the display may be dynamically updated to display the most current data collection over the time period.

Additionally, the ventilator 102 may be capable of detecting an anomaly in connection with a variety of potential issues based on an analysis of the waveform. For example, the ventilator 102 may detect a feature of the waveform that is statistically significant or that is an anomaly. Statistical significance may be determined with respect to an outlier of the data associated with the patient 106, an outlier of data accumulated from multiple patients, or similarity to data retrieved from a database representing specific problems or issues encountered during ventilation. After an anomaly is detected, the ventilator 102 may analyze a section of a waveform surrounding the anomaly to determine a relationship or association with a potential issue. For example, potential issues that may be associated with the waveform include flow starvation, tachypnea, Auto-PEEP, or any other potential issue arising out of ventilation. After an anomaly is detected, the ventilator 102 may automatically take a screen capture (or still image) of the waveform including the feature identified as the anomaly and may issue a notification on the display 110. Additionally or alternatively, the ventilator 102 may issue a variety of other icons, notifications, windows, or other display features on display 110 to assist the clinician 108 in identifying the occurrence of the anomaly. In some cases, when the anomaly is detected that does not require review by clinician 108, the ventilator 102 may automatically adjust one or more settings to mitigate or remedy the potential issue identified, and may display a notification of the adjustments to the one or more settings on the display 110 to be later viewed by a clinician 108.

Figure 2:
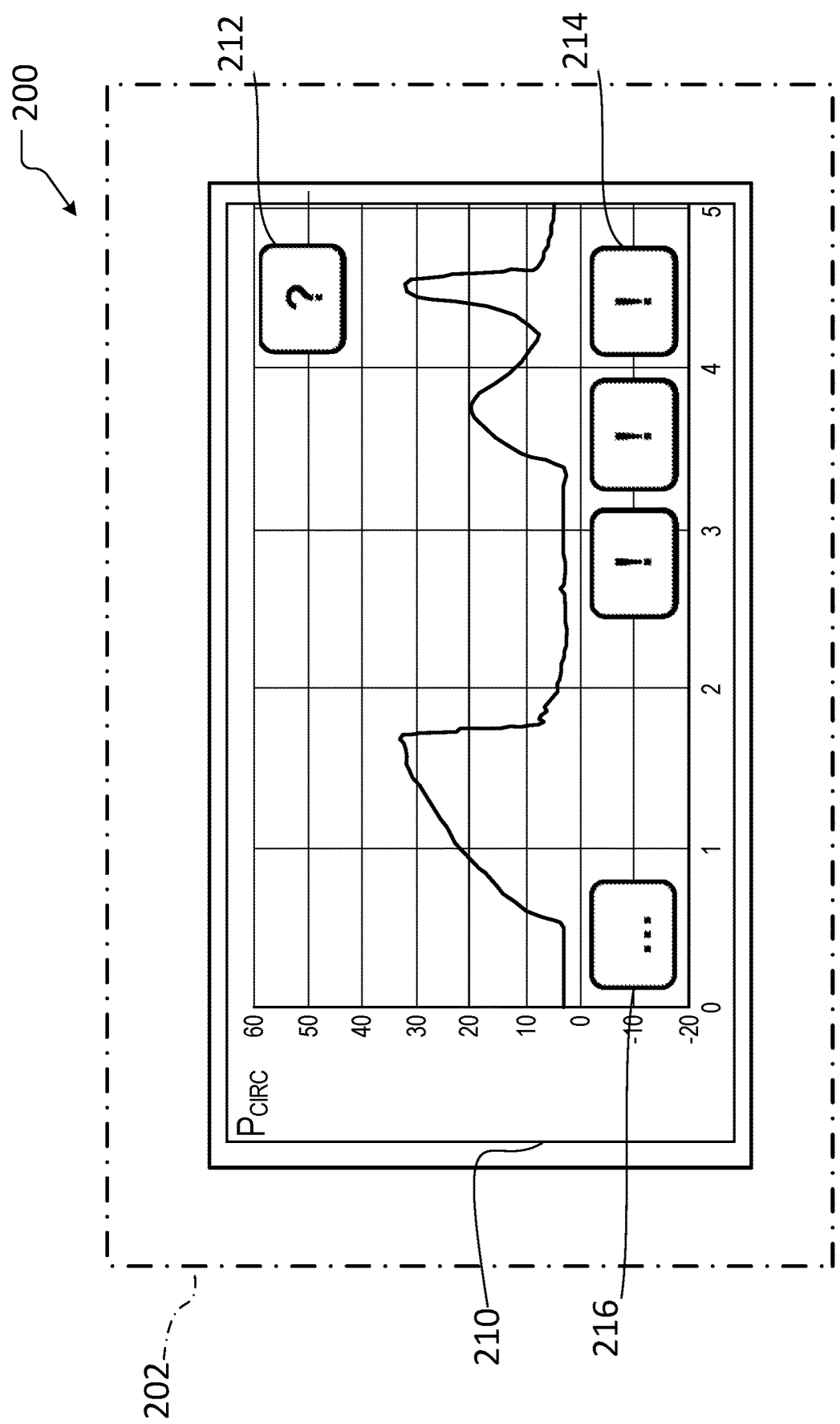
FIG. 2 is an illustration of a ventilator displaying a monitoring window, in accordance with aspects of the disclosure.

FIG. 2 shows one of various windows that may be displayed on a display 202 of a ventilator system 200. As illustrated, a monitor window 210 is provided, the monitoring window 210, including a teaching icon 212, one or more anomaly detection icons 214, and/or supplemental inquiry icon 216. In some aspects, a single education icon may be displayed and may launch any or all of the functionality described with respect to icons 212, 214, and/or 216. The monitor window 210 shows a dynamically updated waveform as a function of time (or other parameter) as a patient, such as patient 106, is monitored by the ventilator system 200. The first window, or monitoring window 210, may be always available and dynamically updated with current patient data. In the present embodiment, the waveform is displayed as pressure versus time, however, the waveform may be expressed as any other parameter measured or calculated by the ventilator system 200 as a function of time or another parameter (e.g., volume). The monitor window 210 may be the only window displayed on the display 202, or alternatively, may be displayed alongside, overtop of, or in addition to other windows containing the same or different waveforms or other patient data.

For purposes of this disclosure, the functionality of an education icon is described in terms of sub-components, including icons 212, 214 and/or 216. However, to avoid clinician confusion, a single education icon may be displayed at all times, or upon detection of an anomaly. In some cases, an education icon may be displayed for each detected anomaly; in other cases, a single education icon may be displayed upon detection of multiple anomalies. In aspects, the functionality of icons 212, 214, 216 may be associated with multiple different user interface buttons, or may be integrated into one user interface button as sub-options. These icons 212, 214, 216 may positioned at any location on the monitor window 210 or on the display 202 as one or more user interface buttons or physical buttons. In some examples, e.g., when the clinician is aware of the anomaly, icons 212, 214, 216 may be disabled by the clinician and may not be displayed upon detection of an anomaly.

A selection of the teaching icon 212 may display a teaching graphic on the monitor window 210 associated with features of the waveform. That is, a clinician may select teaching icon 212 at any time to receive information regarding the various features of the real-time waveform, including identification of inspiratory peak pressure, PEEP, exhalation time, various trigger points, and the like. The teaching graphic may comprise labels, identifiers, other icons, or any other user interface element associated with a specific portion or feature of the waveform being displayed in real-time on the display 202. For example, such labels, identifiers, etc., may be provided as an overlay on the waveform. Additionally, teaching icon 212 may be toggled on and off to show and hide teaching graphics associated with the waveform. In some cases, teaching graphics shown on the monitoring window 210 may be used by a clinician in the room at the time of anomaly detection for quick response.

As further illustrated, one or more anomaly detection icons 214 may be associated with one or more features of the waveform identified by the ventilator system 200 as indicative of one or more anomalies. In aspects, upon identification of an anomaly, ventilator system 200 may capture a screenshot of the waveform including the one or more features indicative of the anomaly. In some aspects, an anomaly detection icon 214 may be provided at or near the feature indicative of the anomaly in the waveform (not shown). A selection of an anomaly detection icon 214 may result in opening new window (e.g., illustrated by FIGS. 4*a*-4*c*) that provides the capture of the waveform associated with the detected anomaly. The time period surrounding the capture may be set, adaptable, or specified to a period that provides a clinician with enough information to recognize the feature or features indicative of the anomaly. For example, upon selecting an anomaly detection icon 214, a new window may open that includes the capture of the waveform for a period of two breaths surrounding or including the anomaly. The new window may be displayed on the display 202 alongside, overtop of, in place of, split-screen with, or any other combination or appearance with the monitoring window 210.

In further aspects, a supplemental inquiry icon 216 may be provided on display 202. In response to selection of supplemental inquiry icon 216, additional information regarding a detected anomaly may be provided, including links to scholarly articles regarding the anomaly, other patient data collected at the time of anomaly detection in the waveform, patient data collected before, during, or after anomaly detection in the waveform, sample waveforms associated with the anomaly from a population of patients, suggestions for mitigating or remedying a potential issue associated with the anomaly, and the like. As should be appreciated, supplemental inquiry icon 216 may provide any additional information that would be helpful to the clinician for understanding, identifying, and/or mitigating the detected anomaly or similar anomalies detected in the future.

Figure 3A:
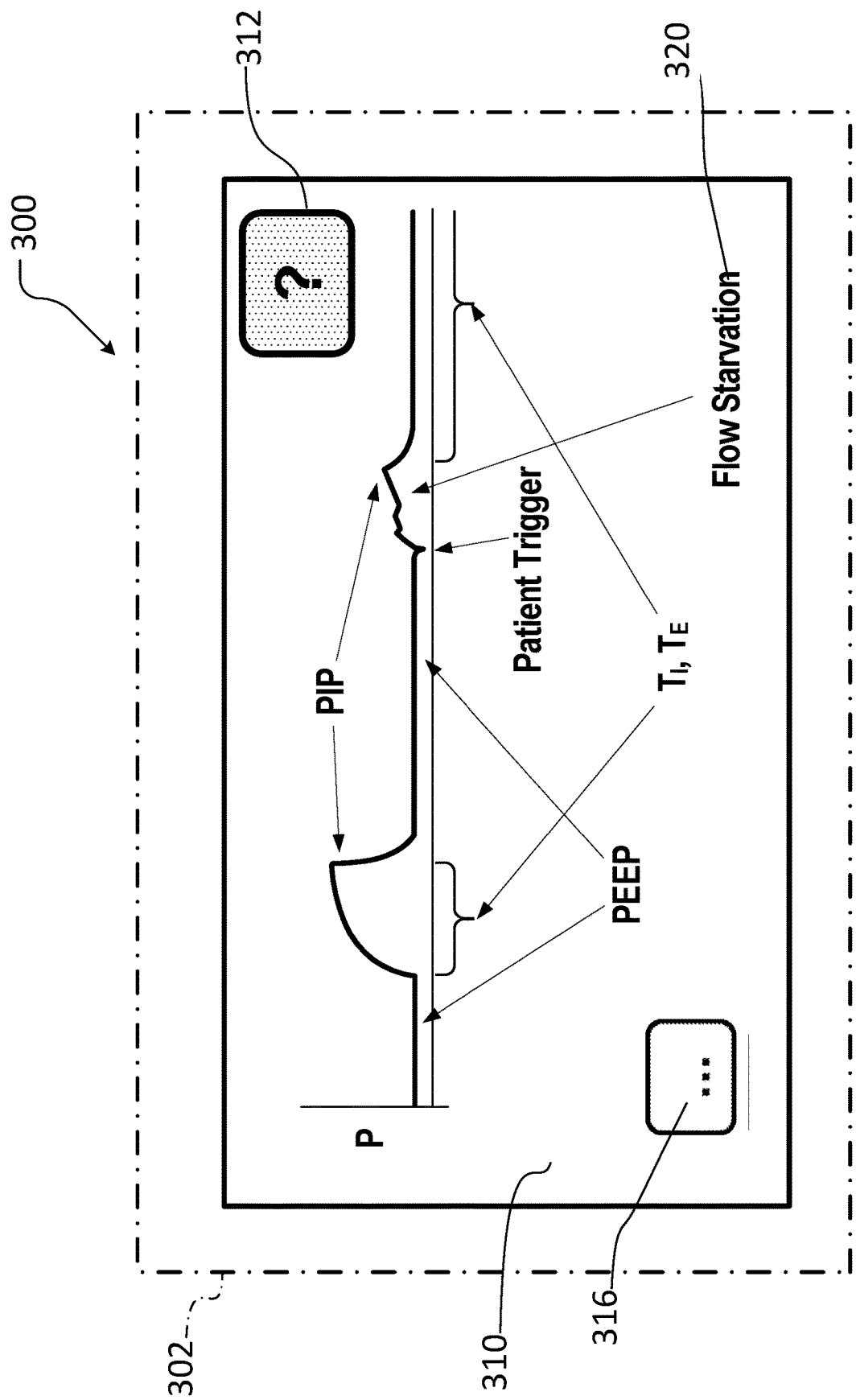
FIG. 3a is the illustration of FIG. 2 including labels of features of the graphic that are associated with a detected anomaly in a monitoring window, in accordance with aspects of the disclosure.

FIG. 3*a* is a further illustration of FIG. 2 that shows an embodiment of ventilator system 300 for the selection of a teaching icon 312, including a teaching graphic 320 associated with a feature of a waveform indicative of an anomaly, in a monitoring window 310. As shown, ventilator system 300 comprises a display 302, a monitoring window 310, a teaching icon 312, and a teaching graphic 320. In this embodiment, the teaching icon 312 is selected/toggled on to display a teaching graphic 320 on the waveform in monitoring window 210. For instance, in response to selection of teaching icon 312, labels, identifiers, other icons, or any other user interface element, are associated with a specific portion or feature of the waveform being displayed in real time on the display 302. In some cases, the teaching icon 312 may be selected at any time during ventilation of a patient and, in response to selection of the teaching icon 312, the ventilator system 300 may display the teaching graphic 320 as an overlay on the waveform. In other cases, a clinician may observe what appears to be an anomaly on the waveform and may select the teaching icon 312 to obtain additional information regarding the anomaly.

As illustrated by FIG. 3*a*, the teaching graphic 320 labels a feature of the waveform associated with a "flow starvation" anomaly. Additionally, teaching graphic 320 labels other features of the waveform, including Positive End Expiratory Pressure (PEEP), inspiratory time ($T_I$), expiratory time ($T_E$), peak inspiratory pressure (PIP), and a patient trigger (e.g., associated with inspiration of the second displayed breath). The teaching graphic 320, shown in the monitoring window 310, may be used by a clinician in the room (or at a remote monitoring device) at the time of anomaly detection (e.g., detection of flow starvation) in order to receive substantially immediate information regarding the anomaly. For example, the clinician may observe an irregular inspiration and, in response to selection of the teaching icon 312, teaching graphic 320 may inform the clinician that the irregular waveform feature is associated with flow starvation. The teaching icon 312, as used in this embodiment, is limited to showing teaching graphic 320 associated with features of the waveform that are currently available in the monitoring window 310. Although the only icon shown in this embodiment is teaching icon 312, other icons may be available in the monitoring window 310, or in other windows, of the display 302.

Figure 3B:
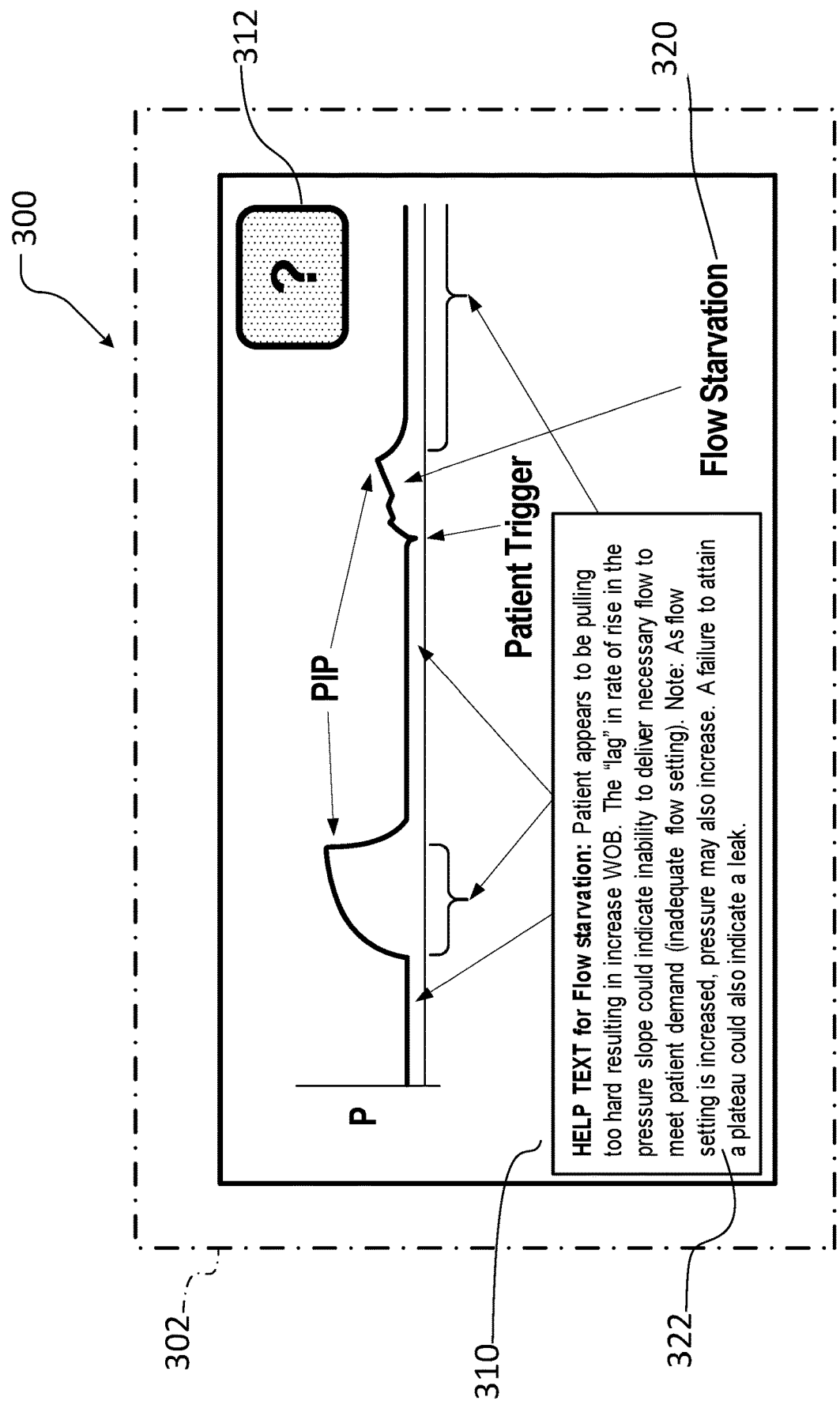
FIG. 3b is the illustration of FIG. 3a further including an annotation that provides educational information associated with the detected anomaly in a monitoring window, in accordance with aspects of the disclosure.

FIG. 3*b* is a further illustration of FIG. 3*a* that shows an embodiment of ventilator display system 300 for the selection of both a teaching icon 312 and a supplemental inquiry icon 316, including a teaching graphic 320 and supplemental text 322 that provides links to external sources of information (not shown), patient data collected at the time of the anomaly (not shown), suggestions for mitigating or remedying issues associated with the detected anomaly (shown), and the like, in a monitoring window 310. As shown, ventilator system 300 comprises a display 302, a monitoring window 310, a teaching icon 312, a supplemental inquiry icon 316, a teaching graphic 320, and supplemental text 322.

In addition to, or in lieu of, a selection of the teaching icon 312, the supplemental inquiry icon 316 may be selected. When selected, the supplemental inquiry icon 316 may cause the display of supplemental text 322 on the monitoring window 310, or alternatively in a different window. The supplemental text 322 may contain links to external sources of information, patient data collected at the time of an anomaly, suggestions for mitigating or remedying a potential issue, statistical analysis for matching the anomaly with the potential issue, a confidence interval, a list of multiple potential issues, a description of one or more potential issues, or any other text or image that may be helpful to educate the clinician regarding a potential problem or problems associated with a detected anomaly. To avoid obscuring the waveform or other patient data provided by monitoring window 310, the supplemental text 322 may be provided as a translucent overlay, may be provided along a border of the monitoring window 310, or may be provided for a time period after which the supplemental text 322 is removed. Additionally or alternatively, the supplemental text 322 may be resized to enlarge display of the supplemental text 322, or reduce display to prevent obscuring other data. In some cases, the supplemental text 322 may be associated with features of the waveform that are currently available in the monitoring window 310; in other cases, supplemental text 322 may remain available in the monitoring window 310 after the anomaly is no longer viewable on the waveform. Although the teaching icon 312 and the supplemental inquiry icon 316 are shown in this embodiment, other icons may be available in the monitoring window 310, in other windows, or generally on the display 302, and the teaching icon 312 may appear without the supplemental inquiry icon 316. In this case, upon selection of the teaching icon 312, teaching graphic 320 may provide icons or other user interface elements for retrieving supplemental information regarding an anomaly or other features of the waveform.

Figure 4A:
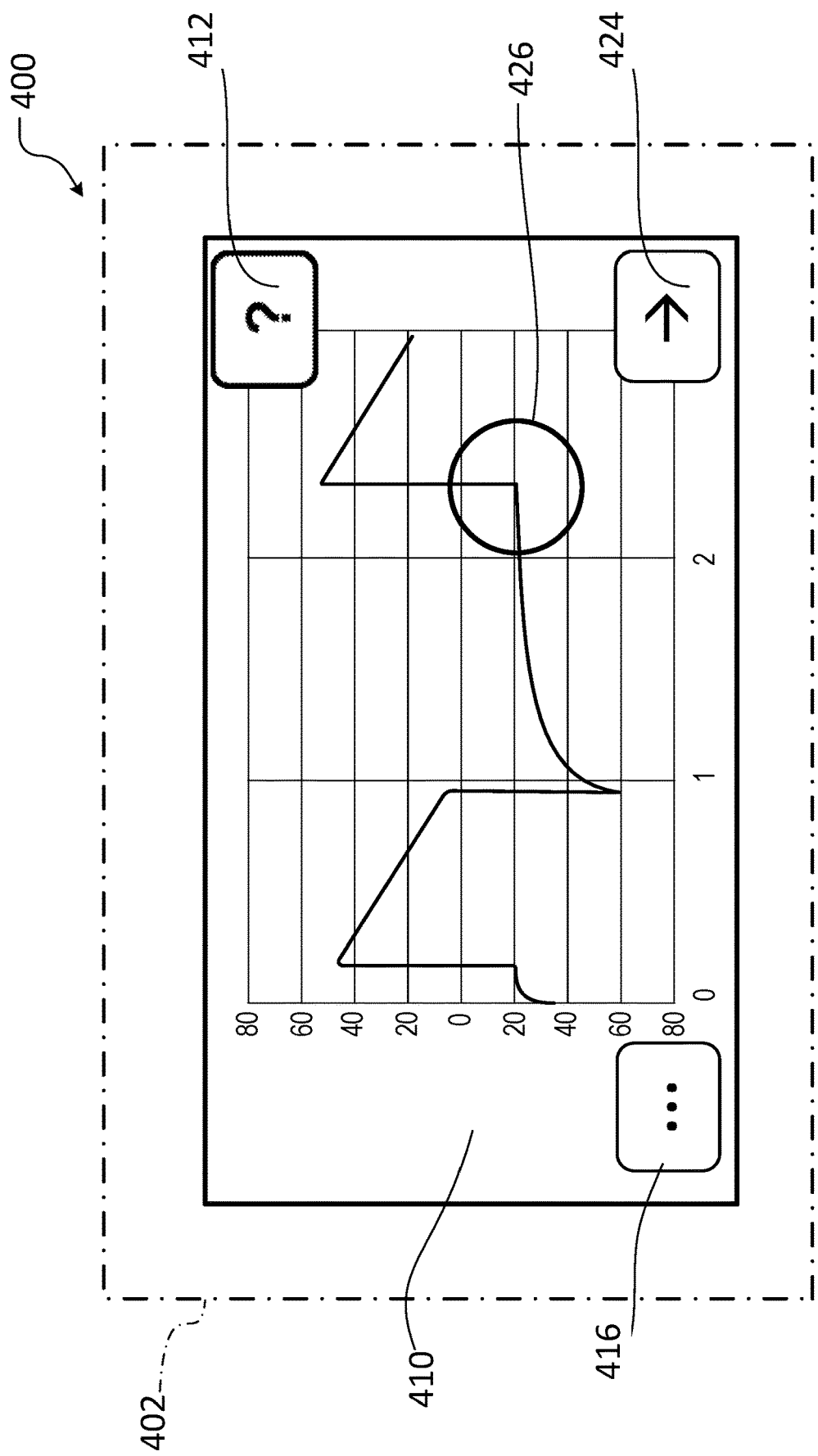
FIG. 4a is an illustration of a capture of a waveform displayed in a capture display window, in accordance with aspects of the disclosure.

FIG. 4*a* is an illustration of ventilator display system 400 showing a capture of a waveform displayed in a capture display window 410, separate from a monitoring window, such as monitoring windows 210, 310. As shown, ventilator system 400 comprises a display 402, a capture display window 410, a teaching icon 412, a supplemental inquiry icon 416, and a return icon 424. The capture display window 410 shows a capture of a portion of a waveform that was, or is still, displayed on a monitoring window, such as a monitoring window 210, 310, separate from the capture display window 410. In the present embodiment, the waveform is displayed as flow versus time, however, the waveform may be expressed as any other parameter measured or calculated by the ventilator system 400 as a function of time or another parameter (e.g., volume), and may or may not be the same parameter viewed in the contemporaneous monitoring window.

The capture display window 410 may be the only window displayed by display 402, or alternatively, may be displayed alongside, overtop of, or in addition to other windows containing the same or different waveforms in the form of a capture or in a monitoring window. For example, a first window, such as a monitoring window, may be displayed concurrently with a second window, such as capture display window 410. If the capture display window 410 obstructs one or more other concurrently displayed windows, the return icon 424 may be used to bring the window forward or backward or to return to the previous main screen. The waveform capture displayed in the capture display window 410 may be a freeze frame, image, animation, or any other display format for memorializing a portion of a waveform associated with a previous time period. For instance, in response to detection of an anomaly, the ventilator system 400 may automatically capture a portion of a waveform including features indicative of the anomaly and the waveform capture may be saved to memory of ventilator system 400. In some cases, the ventilator system 400 may capture an entire waveform, a set of waveforms, or portions of multiple waveforms including features indicative of the detected anomaly (e.g., portions of a pressure waveform, a pressure-volume loop waveform, a flow waveform, and the like). The period of time associated with the portion(s) of the waveform captured may be any period of time and may be pre-set or automatically determined, e.g., based on the detected anomaly, the particular waveform captured, or otherwise.

Similar to monitoring window 210, 310, various icons may be displayed on the capture display window 410, including but not limited to a teaching icon 412, a supplemental inquiry icon 416, and a return icon 424. Additionally, an indicator 426 identifying the detected anomaly (in this case, air trapping) on the waveform may be provided. The indicator may include any suitable graphical element for bringing attention to the anomaly. As shown, indicator 426 is a circle graphical element identifying the anomaly on the waveform, but indicator 426 may be an asterisk near the anomaly, a different-colored portion of the waveform, or any other indicator. In the illustrated case, an anomaly detection icon is not displayed (e.g., because capture display window 410 was launched in response to selection of an anomaly detection icon from a monitoring window 210, 310). These icons 412, 416, and/or 424 may be displayed in the capture display window 410, or may be generally associated with options provided in one or more other windows concurrently available on the display 402. Additionally or alternatively, the functions of icon 412, 416, 424 may be associated with multiple different user interface buttons, integrated into one user interface button as sub-options, or combined into one or more user interface buttons that perform multiple functions when toggled on/off. These icons 412, 416, 424 may positioned at any location on the capture display window 410 or on other windows provided by the display 402 as user interface buttons or physical buttons.

A selection of the teaching icon 412 may display a teaching graphic on the capture display window 410 associated with features indicative of anomalies identified on the waveform. The teaching graphic may comprise labels, identifiers, other icons, or any other user interface element associated with a specific portion or feature of the captured waveform being displayed on the capture display window 410, and may be viewable as a still image or may be animated depending on the format of the capture. Teaching icon 412 may be toggled on and off to show and hide teaching graphics associated with the captured portion of the waveform.

A selection of the supplemental inquiry icon 416 may display supplemental text on the capture display window 410, or alternatively in a different window, and may include: a description of the anomaly, a description of a potential patient condition or change in patient condition associated with the anomaly; one or more potential causes of the anomaly; links to scholarly articles regarding the anomaly; other patient data collected at the time of anomaly detection in the waveform; one or more sample waveforms associated with the anomaly from a population of patients; a suggestion for mitigating a potential issue with the ventilation of the patient associated with the anomaly; and/or any other text or image that may be helpful to educate the clinician regarding a potential problem or problems associated with a detected anomaly.

Figure 4B:
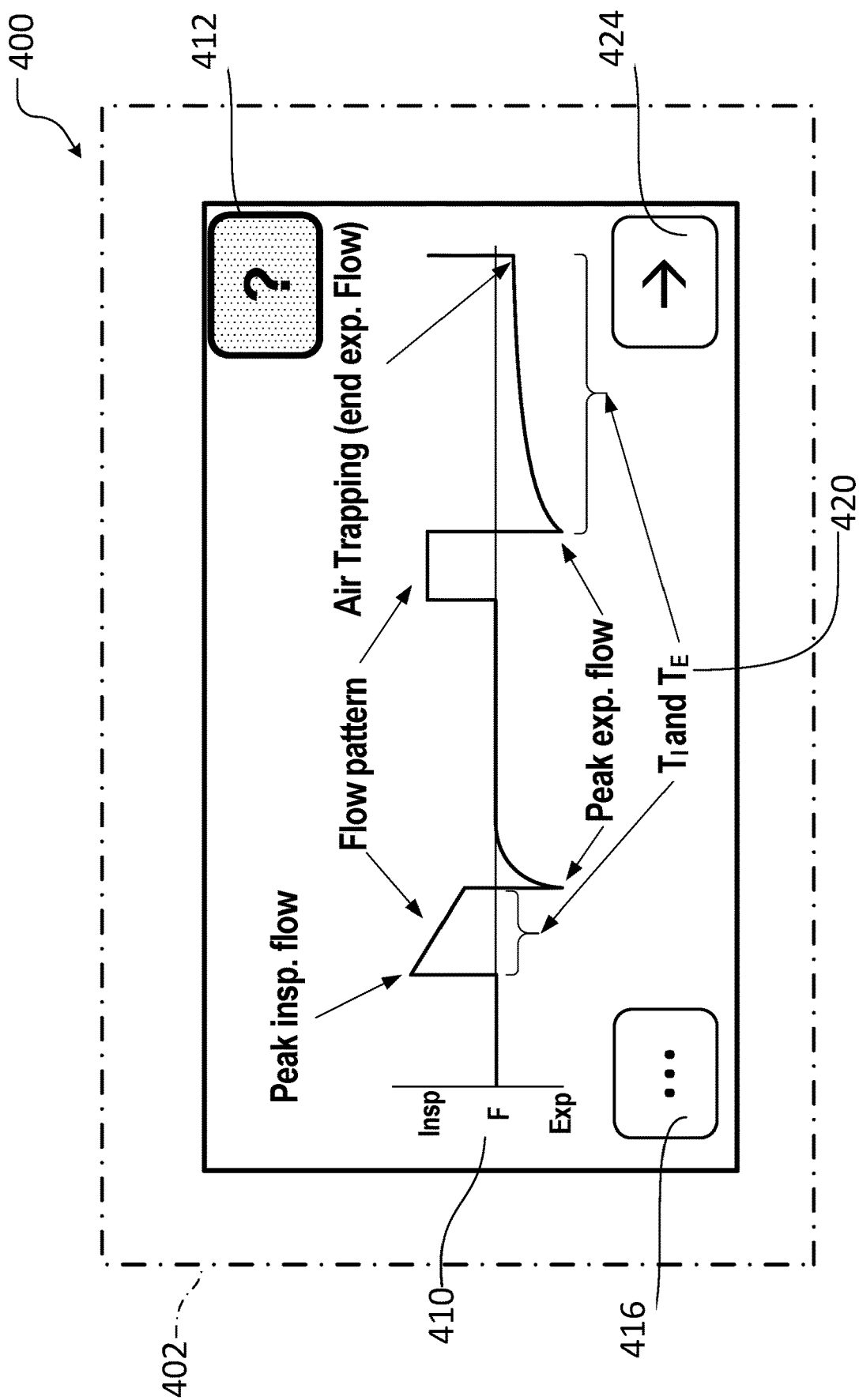
FIG. 4b is the illustration of FIG. 4a further including labels of features of the captured waveform in the capture display window, in accordance with aspects of the disclosure.

FIG. 4b is a further illustration of the ventilator display system 400 of FIG. 4a, with a selection of the teaching icon 412 and accompanying teaching graphic 420. As shown, ventilator display system 400 comprises a display 402, a capture display window 410, a teaching icon 412, a supplemental inquiry icon 416, a return icon 424, and a teaching graphic 420. In this embodiment, the teaching icon 412 is selected/toggled on (shown by shading) to display the teaching graphic 420 on the capture display window 410. For instance, in response to selection of the teaching icon 312, labels, identifiers, other icons, or any other user interface element, are provided to annotate specific portions or features of the captured waveform. Although the teaching icon 412 and the supplemental inquiry icon 416 are shown in this embodiment, other icons may be available in the capture display window 410, in other windows, or on the display 402, and the teaching icon 412 may appear without the supplemental inquiry icon 416. In some cases, the teaching icon 412 may be selected at any time during ventilation of a patient and, in response to selection of the teaching icon 412, the ventilator system 400 may display the teaching graphic 420 as an overlay on the waveform. In other cases, a clinician may observe what appears to be an anomaly on the waveform and may select the teaching icon 412 to obtain additional information regarding the anomaly. In still other examples, a clinician may select a portion of the waveform (e.g., by touching the display at a point on the waveform) to launch the teaching graphic 420. In this case, the point on the waveform may be "normal" (e.g., normal end expiratory flow without air trapping) and the teaching graphic 420 may provide information regarding this normal condition. In other cases, the point on the waveform may be an "anomaly" (e.g., end expiratory flow did not reach baseline with some air trapping) and the teaching graphic 420 may provide descriptive information regarding the anomaly. In this way, the clinician may learn to recognize both normal and abnormal portions of the waveform by touching the display and/or selecting the teaching icon 412.

As illustrated by FIG. 4b, the teaching graphic 420 labels a feature of the waveform associated with an "auto positive end expiratory pressure (Auto-PEEP)" anomaly (also known as "intrinsic PEEP" or "air trapping"). Additionally, teaching graphic 420 labels other features of the waveform, including peak inspiratory flow, flow pattern, air trapping (indicated by end expiratory flow less than zero), peak expiratory flow, inspiratory time ($T_I$), and expiratory time ($T_E$). For instance, when the ventilator detects the anomaly (e.g., air trapping or "Auto-PEEP"), the teaching graphic 420, shown in the monitoring window 410, may be used by a clinician viewing capture display window 410 to receive substantially immediate information regarding the anomaly. For example, in some cases, the clinician may be treating other patients and may not observe an irregular inspiration in real time. In this case, the irregular inspiration may not breach an alarm threshold, thereby alerting the clinician with an audible or visual alarm, but may instead display an anomaly detection icon. When the clinician returns to monitor the patient, or at a later time, the clinician may select an anomaly detection icon to view a capture of the waveform including the anomaly on capture display window 410. In response to selection of the teaching icon 412, teaching graphic 420 may inform the clinician of an irregular feature associated with the anomaly on the waveform capture. In other aspects, upon selecting the anomaly detection icon to launch the capture display window 410, the teaching graphic may be displayed on the waveform capture without the need to select a teaching icon 412.

Figure 4C:
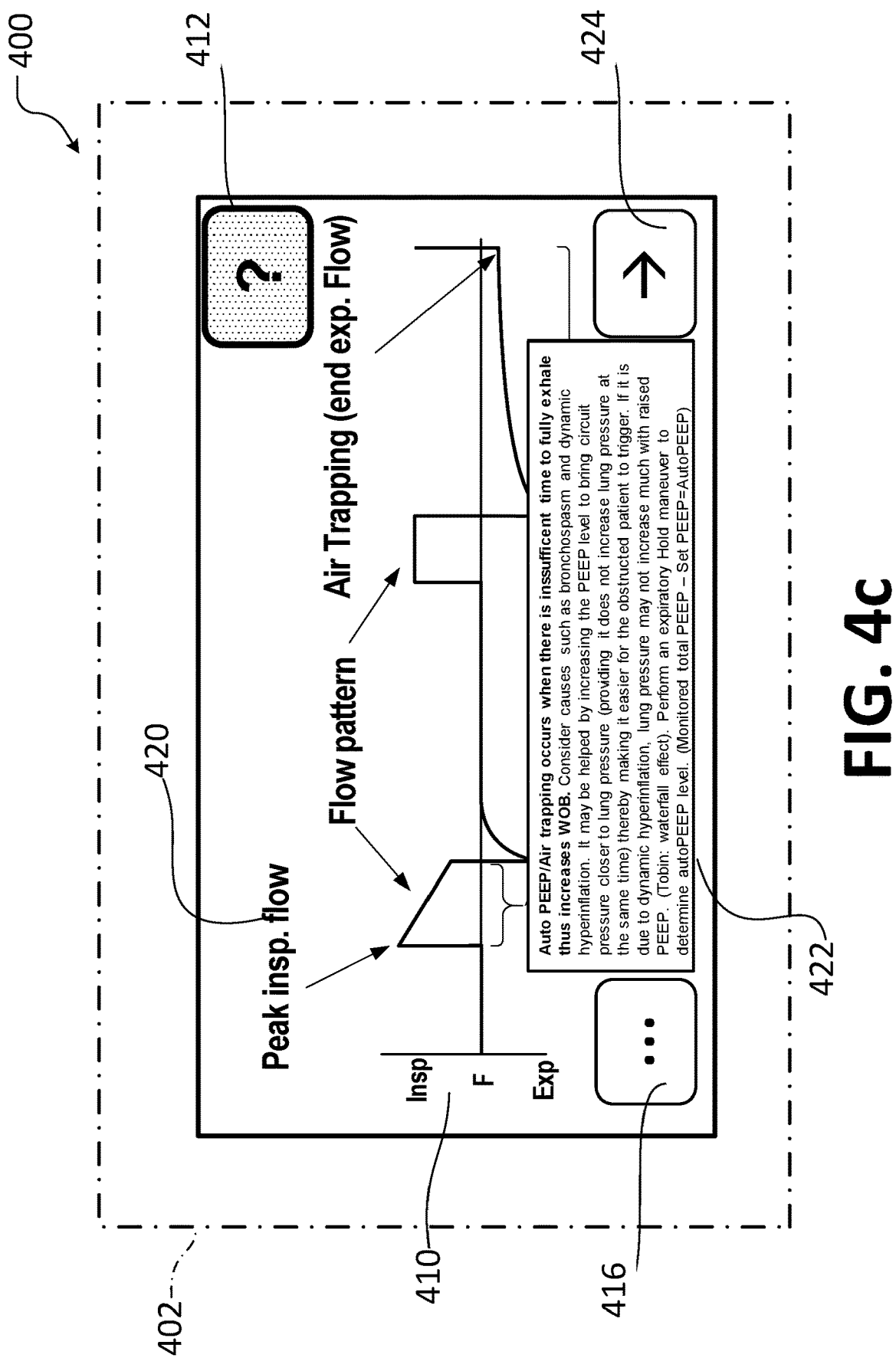
FIG. 4c is the illustration of FIG. 4b further including supplemental text that provides educational information associated with the labelled features of the captured waveform in the capture display window, in accordance with aspects of the disclosure.

FIG. 4c is a further illustration of the ventilator display system 400 of FIG. 4b, with a selection of both the teaching icon 412 and a supplemental inquiry icon 416, displaying an accompanying teaching graphic 420 and supplemental text 422. As shown, ventilator display system 400 comprises a display 402, a capture display window 410, a teaching icon 412, a supplemental inquiry icon 416, a return icon 424, and a teaching graphic 420. In addition to, or in lieu of, a selection of the teaching icon 412, the supplemental inquiry icon 416, as shown in this embodiment, may also be selected. When selected, the supplemental inquiry icon 416 may cause the display of supplemental text 422 on the capture display window 410, or alternatively in a different window. The supplemental text 422 may contain links to external sources of information, patient data collected at the time of an anomaly, suggestions for mitigating or remedying a potential issue, statistical analysis for matching the anomaly with the potential issue, a confidence interval, a list of multiple potential issues, a description of one or more potential issues, or any other text or image that may be helpful to educate the clinician regarding a potential problem or problems associated with a detected anomaly. To avoid obscuring the waveform or other patient data provided by capture display window 410, the supplemental text 422 may be provided as a translucent overlay, may be provided along the border of the capture display window 410, may be provided for a time period after which the supplemental text 422 is removed, or may be manually "pinned" to the user interface display (e.g., by selecting a "push pin icon," not shown) for convenient clinician reference.

Additionally or alternatively, the supplemental text 422 may be resized to prevent obscuring other data. In some cases, the supplemental inquiry icon 416, is associated with features of the waveform that are in the capture display window 410. Although the teaching icon 412 and the supplemental inquiry icon 416 are shown in this embodiment, other icons may be available in the capture display window 410, in other windows, or generally on the display 402, and the supplemental inquiry icon 416 may appear without the teaching icon 412. In this case, upon selection of the teaching icon 412, teaching graphic 420 may provide icons or other user interface elements for retrieving supplemental information regarding the anomaly or other features of the captured waveform. Alternatively still, the teaching graphic 420 and/or the supplemental text 422 may be displayed in the capture display window 410 in response to selection of an anomaly detection icon and may not require selection of additional icons, including teaching icon 412 and/or supplemental inquiry icon 416.

Figure 5:
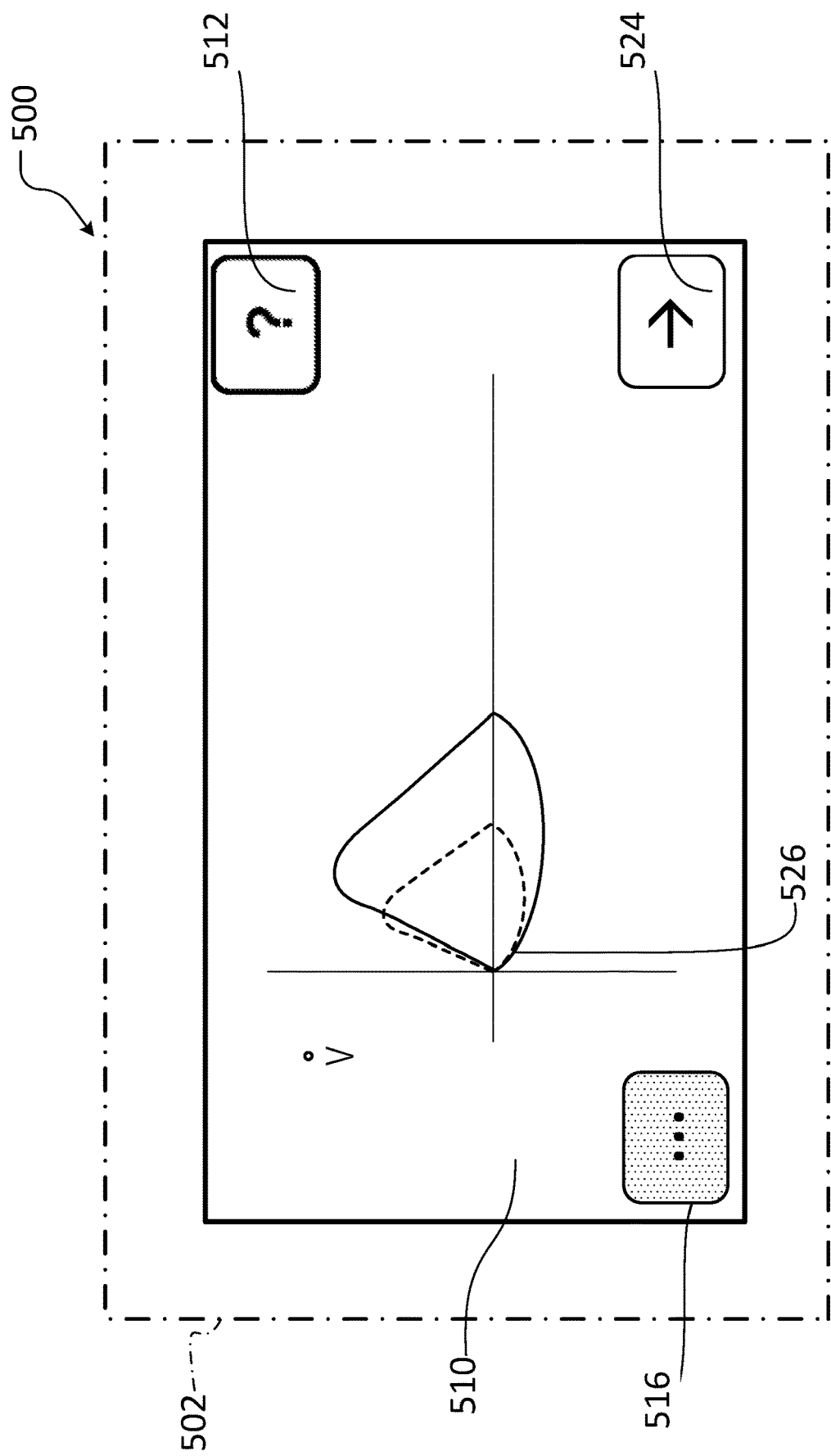
FIG. 5 is an illustration of overlaying a capture of a waveform over a second waveform, in accordance with aspects of the disclosure.

FIG. 5 is an illustration of overlaying a capture of a waveform over a second waveform. As shown, ventilator system 500 comprises a display 502, a capture display window 510, a teaching icon 512, a supplemental inquiry icon 516, and a return icon 524.

In further aspects, a supplemental inquiry icon 516 may be provided on display 502. In response to selection of supplemental inquiry icon 516, additional information regarding a detected anomaly may be provided, including links to scholarly articles regarding the anomaly, other patient data collected at the time of anomaly detection in the waveform, sample waveforms associated with the anomaly from a population of patients, suggestions for mitigating or remedying a potential issue associated with the anomaly, and the like. As should be appreciated, supplemental inquiry icon 516 may provide any additional information that would be helpful to the clinician for understanding, identifying, and/or mitigating the detected anomaly or similar anomalies detected in the future.

As an example, a first window that contains a first waveform may overlay a second window that contains a second waveform. The first waveform and the second waveform may include any one or more of the following: a capture of a waveform, a dynamically updated waveform, a waveform aggregated based on data from a population of patients, a waveform stored or statistically modeled from a database, a waveform modeling data from a normal state of the patient, a waveform comparison between waveforms exhibiting a normal state and an anomaly state of the patient, or any other waveform related to patient ventilator data. The first window and the second window may be the same window or two different windows, including a monitoring window, such as monitoring window 210, a capture display window, such as capture display window 410, or any other window viewable on ventilator system 500.

As a further example, capture display window 510 may be compared with a second waveform by being displayed alongside, overtop of (e.g., in a translucent window), or in addition to a second waveform. This comparison may be made in the same window or in separate windows of the display 502, and may consist of a variety of waveforms. As an example, the capture of the waveform displayed by a solid line in the capture display window 510 may be overlaid with a second waveform displayed by a dashed line in the capture display window 510. The second waveform may be selected from a variety of different sources, including but not limited to a statistically-based waveform associated with a recognized anomaly, real-time waveform data for the current patient, a patient-specific waveform captured at a different time than the time of anomaly detection, "normal" patient data collected either from multiple patients or for the current patient, and the like. This data may be stored in a local memory in the display 502, or on an external device.

Figure 6:
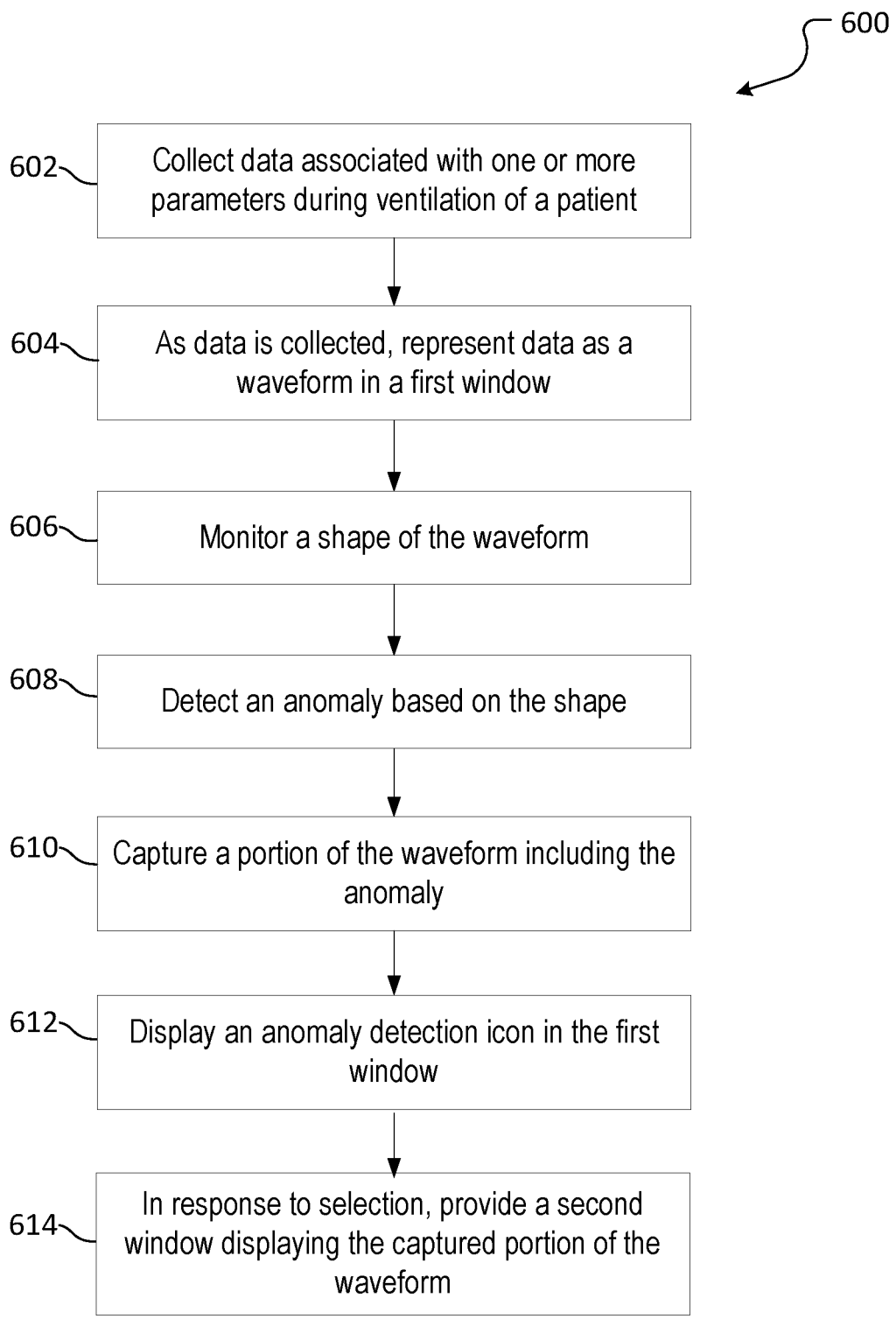
FIG. 6 is a flow diagram illustrating a method for clinician decision support during mechanical ventilation of a patient with a ventilator, in accordance with aspects of the disclosure.

FIG. 6 is a flow diagram illustrating a method for clinician decision support during mechanical ventilation of a patient with a ventilator. In an example, method 600 may be performed by a ventilator, such as ventilator 102. Method 600 begins at operation 602, where the ventilator collects data from one or more sensors monitoring one or more parameters during ventilation of a patient. As an example, the ventilator may collect and/or calculate a variety of parameters associated with ventilation of the patient, including but not limited to flow, pressure, and/or volume. Additionally, the ventilator may collect data regarding an inspiratory time ($T_I$), an expiratory time ($T_E$), a peak inspiratory pressure (PIP), an end-expiratory flow (EEF), a positive end expiratory pressure (PEEP), a respiratory rate (RR), an inspiratory/expiratory (I/E) ratio, and the like.

At operation 604, as data is collected, the ventilator may represent the data as a waveform in a first window. For instance, the ventilator may plot data collected (or calculated) for a parameter as a function of time. As the data is collected, the ventilator may dynamically update the waveform to provide a continuous graphical representation of the parameter over time. In aspects, the waveform may graphically represent flow versus time, pressure versus time, volume versus time, flow versus volume, pressure versus volume, or combinations of parameters versus time. Waveforms representing other parameters as a function of time, as well as one parameter versus another parameter, should also be appreciated. As an example, a ventilator display, such as display 202, may display the waveform in a monitoring window, such as monitoring window 210, to enable a clinician to monitor the progress of ventilation of the patient. While other windows may be open or available on the ventilator, operation 604 displays the waveform in at least one window (e.g., a first window) to provide the clinician with a near real-time graphical representation of monitored patient data.

At operation 606, the ventilator monitors a shape and/or characteristics of the waveform. The ventilator may monitor the shape and/or characteristics of the waveform by comparing the waveform to a variety of secondary waveforms, including but not limited to statistical or educational data regarding recognized anomalies and/or "normal" patient data collected either from a patient population or for the current patient. As detailed above, an anomaly is defined as an irregularity in monitored patient data that may not be sufficient to trigger an alarm. A "recognized" anomaly may be an irregularity in monitored patient data that has been characterized across a patient population or disease state and includes one or more identifiable features. In aspects, the one or more identifiable features are associated with a shape (or characteristics) of a waveform representing monitored patient data. The shape (or characteristics) of the waveform may be monitored for correlation to a set of problem data (e.g., characterized across a patient population or disease state), or to identify statistical outliers in monitored patient data, or both, or any other means of waveform analysis to detect anomalies in the data.

At operation 608, the ventilator detects an anomaly based on the shape or characteristics of the waveform monitored in step 606. For instance, an anomaly may be detected when an identifiable feature associated with a recognized anomaly is detected, when a statistically significant outlier in patient data is detected based on monitoring a shape (or characteristics) of the waveform, or otherwise. It should be appreciated that monitoring and detection at operations 608 and 610 may be performed in response to receiving a user selection of an icon that may toggle the anomaly detection feature on and off to save computational resources and storage space for patients in a stable condition. Alternatively, operations 606 and 608 may be continuously performed in the background to detect anomalies in patient data that do not rise to the level of breaching an alarm threshold but that may be indicative of a patient condition or a change in patient condition.

When an anomaly is detected, at operation 610, the ventilator may automatically capture a portion of the waveform including the anomaly. In aspects, "capturing" a portion of the waveform may include automatically recording the portion of the waveform including the anomaly, where recording the portion of the waveform may involve storing the waveform for one or more breaths during which the anomaly occurred. Additionally or alternatively, "capturing" a portion of the waveform may include automatically taking an image or snapshot of the waveform including the anomaly, where the image or snapshot may include one or more breaths during which the anomaly occurred. Additionally or alternatively, "capturing" a portion of the waveform may include automatically storing the data represented by the waveform for a period of time before, during, and after the anomaly detection. A time period for a waveform capture may be set, adaptable, or specified to a period that provides a clinician with enough information to identify a feature of the waveform as an anomaly or outlier in comparison to other features of the waveform. For example, the time period may be defined by a number of breaths, may be defined as a length of time (e.g., in milliseconds, seconds, minutes, etc.), or otherwise. As should be appreciated, capturing the waveform may include any or all of the aspects above, as well as any other suitable method for storing data associated with an anomaly for future evaluation by the ventilator or a clinician.

At operation 612, the ventilator may display an anomaly detection icon. In aspects, the anomoly detection icon may be displayed in the monitoring window (e.g., first window) that displays the waveform in order to alert the clinician that an anomaly was detected. The anomaly detection icon may be displayed in any suitable location within the first window. For example, the anomaly detection icon may be displayed within a banner, ribbon, or tool bar of the first window; along a time axis of the waveform at or near when the anomaly occurred; in a dropdown or other menu; at or near a feature of the waveform associated with the anomaly; and the like. In some cases, an anomaly detection icon may be displayed each time an anomaly is detected, allowing for multiple anomaly detection icons to be displayed when multiple anomalies have been detected. In other cases, a single anomaly detection icon may be displayed after a first anomaly is detected and the single anomaly detection icon may be displayed regardless of the number of subsequent anomalies that are detected. In further aspects, after selection of the anomaly detection icon is received, the anomaly detection icon may be cleared and may no longer be displayed.

At operation 614, in response to receiving a selection of the anomaly detection icon, such as anomaly detection icon 214, the ventilator may open new window (e.g., second window) that displays the captured portion of the waveform including the anomaly. For example, the new window may display a capture of the waveform for a period of two breaths (e.g., the portion of the waveform) including the anomaly. The new window (e.g., second window) may be displayed by the ventilator alongside, overtop of (e.g., as a transparent overlay), in place of, in split-screen with, or any other combination, in the ventilator display, e.g., display 202, with the monitoring window (e.g., the first window) displaying the waveform.

Figure 7:
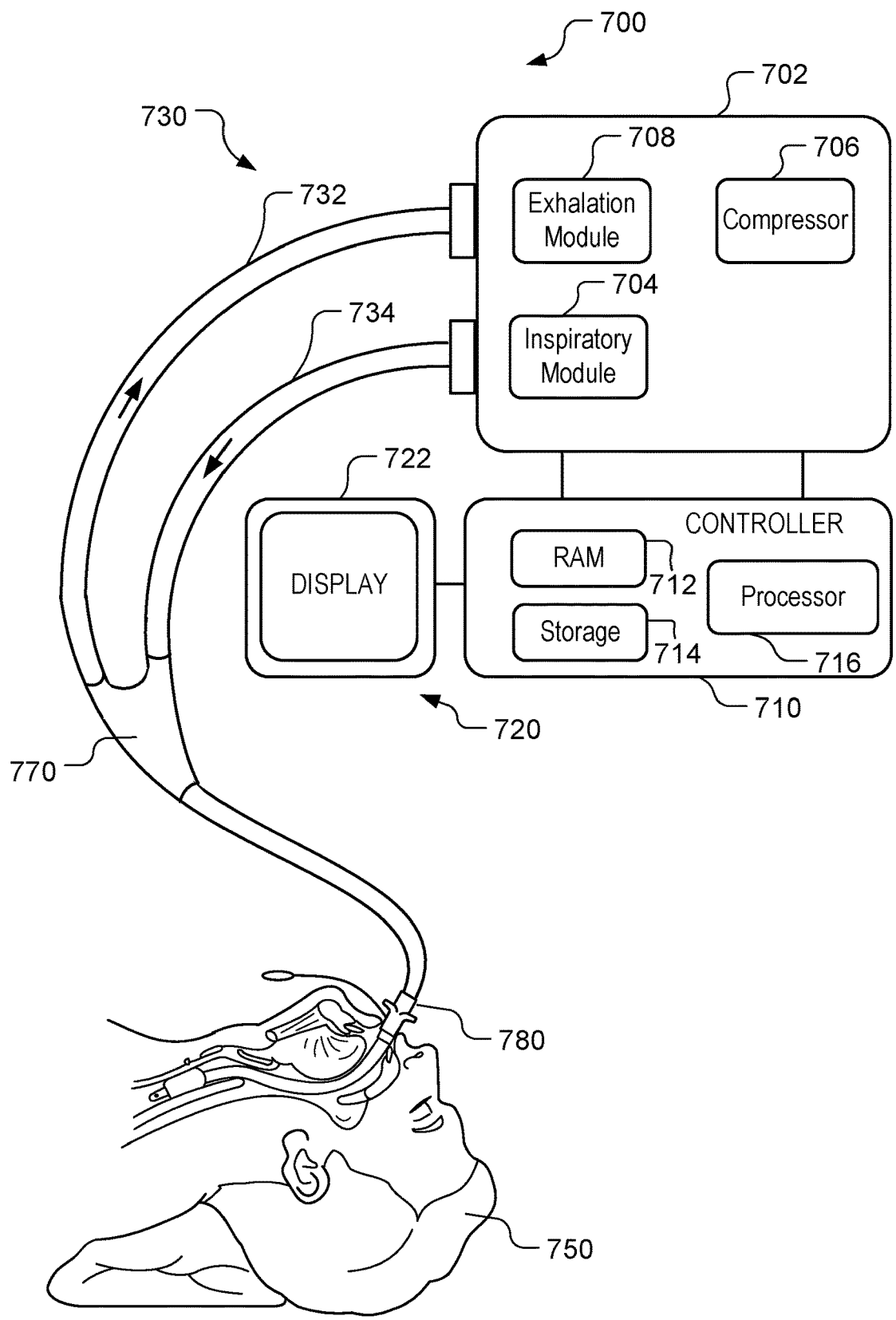
FIG. 7 is a diagram illustrating an embodiment of an exemplary ventilator connected to a human patient.

FIG. 7 is a diagram illustrating an embodiment of an exemplary ventilator 700 connected to a human patient 750. Ventilator 700 includes a pneumatic system 702 (also referred to as a pressure generating system 702) for circulating breathing gases to and from patient 750 via the ventilation tubing system 730, which couples the patient to the pneumatic system via an invasive (e.g., endotracheal tube, as shown) or a non-invasive (e.g., nasal mask) patient interface.

Ventilation tubing system 730 may be a two-limb (shown) or a one-limb circuit for carrying gases to and from the patient 750. In a two-limb embodiment, a fitting, typically referred to as a "wye-fitting" 770, may be provided to couple a patient interface 780 (as shown, an endotracheal tube) to an inspiratory limb 734 and an expiratory limb 732 of the ventilation tubing system 730.

Pneumatic system 702 may be configured in a variety of ways. In the present example, system 702 includes an exhalation module 708 coupled with the expiratory limb 732 and an inhalation module 704 coupled with the inspiratory limb 734. Compressor 706 or other source(s) of pressurized gases (e.g., air, oxygen, and/or helium) is coupled with inhalation module 704 to provide a gas source for ventilatory support via inspiratory limb 734.

The pneumatic system 702 may include a variety of other components, including mixing modules, valves, sensors, tubing, accumulators, filters, etc. Controller 710 is operatively coupled with pneumatic system 702, signal measurement and acquisition systems, and an operator interface 720 that may enable an operator to interact with the ventilator 700 (e.g., change ventilator settings, select operational modes, view monitored parameters, etc.). Controller 710 may include memory 712, one or more processors 716, storage 714, and/or other components of the type commonly found in command and control computing devices. In the depicted example, operator interface 720 includes a display 722 that may be touch-sensitive and/or voice-activated, enabling the display 722 to serve both as an input and output device.

The memory 712 includes non-transitory, computer-readable storage media that stores software that is executed by the processor 716 and which controls the operation of the ventilator 700. In an embodiment, the memory 712 includes one or more solid-state storage devices such as flash memory chips. In an alternative embodiment, the memory 712 may be mass storage connected to the processor 716 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 716. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory system or between the ventilatory system and other therapeutic equipment and/or remote monitoring systems may be conducted over a distributed network, as described further herein, via wired or wireless means. Further, the present methods may be configured as a presentation layer built over the TCP/IP protocol. TCP/IP stands for "Transmission Control Protocol/Internet Protocol" and provides a basic communication language for many local networks (such as intra- or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Figure 8:
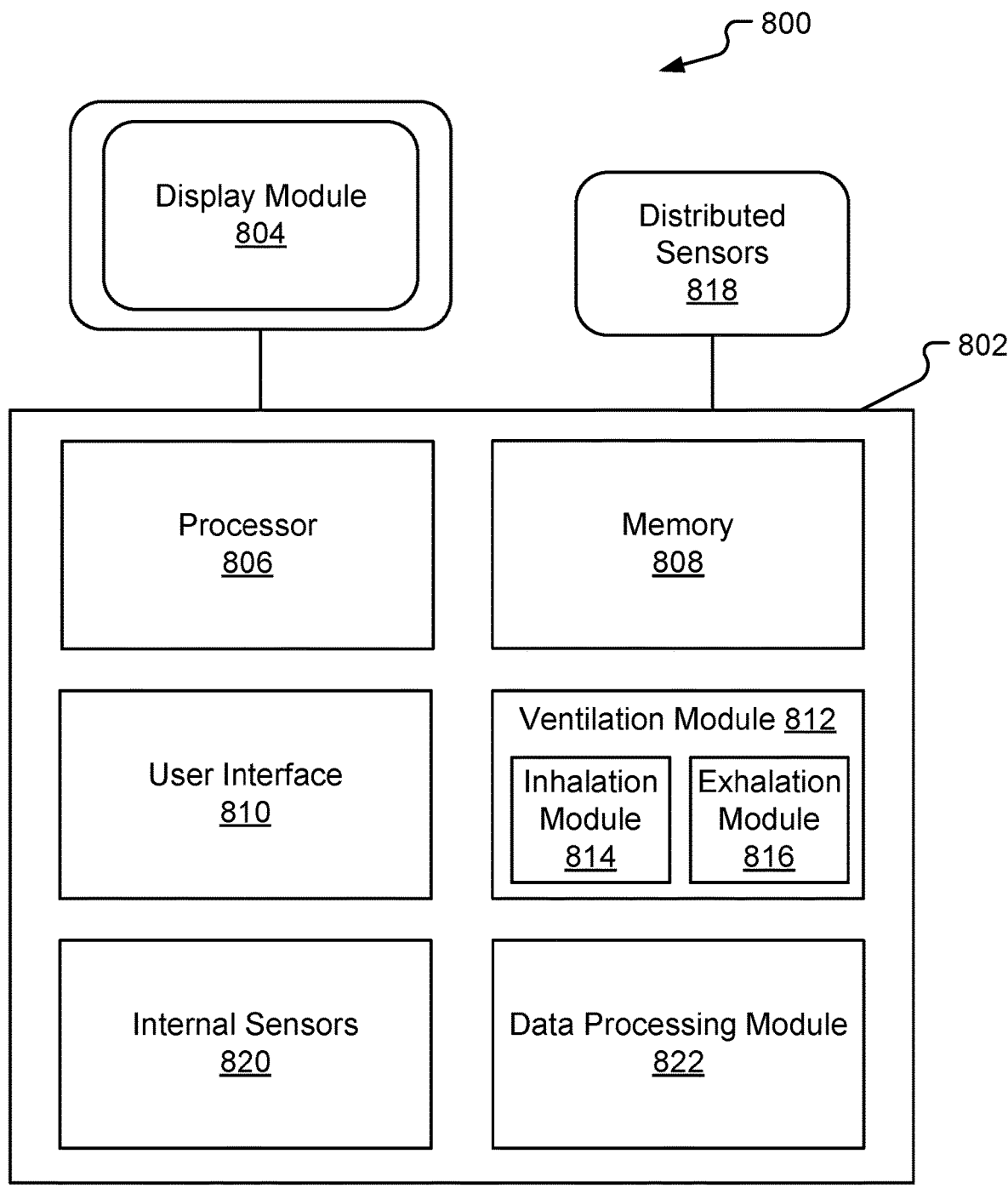
FIG. 8 is a block-diagram illustrating an embodiment of a ventilator system for clinician decision support.

FIG. 8 is a block-diagram illustrating an embodiment of a ventilatory system for clinician decision support. Ventilatory system 800 includes ventilator 802 with its various modules and components. That is, ventilator 802 may further include, inter alia, memory 808, one or more processors 806, user interface 810, and ventilation module 812 (which may further include an inspiration module 814 and an exhalation module 816). Memory 808 is defined as described above for memory 812. Similarly, the one or more processors 806 are defined as described above for one or more processors 816. Processors 806 may further be configured with a clock whereby elapsed time may be monitored by the system 800.

The ventilatory system 800 may also include a display module 804 communicatively coupled to ventilator 802. Similar to display 202, display module 804 provides various input screens, for receiving clinician input, and various display screens, for presenting useful information to the clinician. The display module 804 is configured to communicate with user interface 810 and may include a graphical user interface (GUI). The GUI may be an interactive display, e.g., a touch-sensitive screen or otherwise, and may provide various windows (i.e., visual areas) comprising elements for receiving user input and interface command operations and for displaying ventilatory information (e.g., ventilatory data, alerts, patient information, parameter settings, etc.). The elements may include controls, graphics, charts, tool bars, input fields, icons, etc. Alternatively, other suitable means of communication with the ventilator 802 may be provided, for instance by a wheel, keyboard, mouse, or other suitable interactive device. Thus, user interface 810 may accept commands and input through display module 804. Display module 804 may also provide useful information in the form of various ventilatory data regarding the physical condition of a patient and/or a prescribed respiratory treatment. The useful information may be derived by the ventilator 802, based on data collected by a data processing module 822, and the useful information may be displayed to the clinician in the form of graphs, wave representations (e.g., a waveform), pie graphs, or other suitable forms of graphic display. For example, the data processing module 822 may be operative to detect one or more anomalies by monitoring a shape (or characteristics) of one or more waveforms representing monitored patient data and may display useful information regarding the one or more anomalies in the form of a teaching graphic or supplemental text, as detailed above.

Ventilation module 812 may oversee ventilation of a patient according to ventilatory settings. Ventilatory settings may include any appropriate input for configuring the ventilator to deliver breathable gases to a particular patient, including settings for delivering either mandatory or spontaneous breaths to the patient. Ventilatory settings may be entered by a clinician, e.g., based on a prescribed treatment protocol for the particular patient, or automatically generated by the ventilator, e.g., based on attributes (i.e., age, diagnosis, ideal body weight, gender, etc.) of the particular patient according to any appropriate standard protocol or otherwise. In some cases, certain ventilatory settings may be adjusted to optimize the prescribed treatment, e.g., decreasing a mandatory rate so there is more time for a spontaneous rate in an assist/control-type mode. Other ventilatory settings may include, inter alia, tidal volume ($V_T$), respiratory rate (RR), inspiratory time ($T_I$), inspiratory pressure ($P_I$), pressure support ($P_{SUPP}$), rise time percent (rise time %), expiratory (or exhalation) time ($T_E$), peak flow, flow pattern, etc.

Ventilation module 812 may further include an inspiration module 814 configured to deliver gases to the patient according to prescribed ventilatory settings. Specifically, inspiration module 814 may correspond to the inhalation module 704 or may be otherwise coupled to source(s) of pressurized gases (e.g., air, oxygen, and/or helium), and may deliver gases to the patient. Inspiration module 814 may be configured to provide ventilation according to various ventilatory types and modes, e.g., via volume-targeted, pressure-targeted, or via any other suitable type of ventilation.

According to embodiments, the inspiration module 814 may provide ventilation via a form of volume ventilation. Volume ventilation refers to various forms of volume-targeted ventilation that regulate volume delivery to the patient. Different types of volume ventilation are available depending on the specific implementation of volume regulation. Volume ventilation may include volume-control (VC), volume-assist, or volume assist/control ventilation. Volume control (VC) ventilation may be provided by delivering a set peak flow and flow pattern for a period of time ($T_I$) to deliver a prescribed tidal volume (i.e., set $V_T$) to the patient. For non-spontaneously-breathing patients, a set $V_T$ and inspiratory time ($T_I$) may be configured during ventilation start-up, e.g., based on the patient's predicted or ideal body weight (PBW or IBW). In this case, flow will be dependent on the set $V_T$ and set $T_I$. Alternatively, set $V_T$ and a peak flow and flow pattern may be set such that $T_I$ is a function of these settings. For spontaneously-breathing patients, a set $V_T$ may be configured and the patient may determine $T_I$.

According to alternative embodiments, the inspiration module 814 may provide ventilation via a form of pressure ventilation. Pressure-targeted types of ventilation may be provided by regulating the pressure delivered to the patient in various ways. According to embodiments described herein, pressure support (PS) ventilation and pressure control (PC) ventilation may be accomplished by setting an inspiratory pressure ($P_I$) (or a pressure support level, $P_{SUPP}$) for delivery to the patient. Pressure ventilation may also include volume-targeted-pressure-control (VC+) or volume-targeted-pressure-support (VS) ventilation, in which a set $V_T$ is targeted by calculating and delivering an effective pressure at the patient airway. Furthermore, pressure ventilation may include proportional assist (PA) ventilation, in which a pressure is targeted that is a function of a clinician-selected percent support and PEEP, in view of an estimate of the patient's resistance and elastance and a calculation of tube resistance.

According to embodiments, during volume ventilation or pressure ventilation, the ventilator may display flow waveforms (or flow traces), volume waveforms, and/or pressure waveforms that graphically represent monitored flow, volume, and/or pressure, respectively, over time. In aspects, based on evaluating a shape (or characteristics) of the various waveforms, the ventilator may detect one or more anomalies, which may be indicative of a patient condition or a change in patient condition. When an anomaly is detected, the ventilator may capture at least a portion of the waveform including the anomaly, as described above, and may display an anomaly detection icon to notify the clinician.

Ventilation module 812 may further include an exhalation module 816 configured to release gases from the patient's lungs according to prescribed ventilatory settings. Specifically, exhalation module 816 may correspond to exhalation module 708 or may otherwise be associated with and/or control an exhalation valve for releasing gases from the patient. By way of general overview, a ventilator may initiate exhalation based on lapse of an inspiratory time setting ($T_I$) or other cycling criteria set by the clinician or derived from ventilator settings (e.g., detecting delivery of prescribed $V_T$ or prescribed $P_I$ based on a reference trajectory). Alternatively, exhalation may be cycled based on detection of patient effort or otherwise. Upon initiating the exhalation phase, exhalation module 816 may allow the patient to exhale by opening an exhalation valve. As such, exhalation is passive, and the direction of airflow, as described above, is governed by the pressure gradient between the patient's lungs (higher pressure) and the ambient surface pressure (lower pressure). Although expiratory flow is passive, it may be regulated by the ventilator based on the size of the exhalation valve opening. Indeed, the ventilator may regulate the exhalation valve in order to target set PEEP by applying a number of calculations and/or trajectories.

According to some embodiments, the inspiration module 814 and/or the exhalation module 816 may be configured to synchronize ventilation with a spontaneously-breathing, or triggering, patient. That is, the ventilator may be configured to detect patient effort and may initiate a transition from exhalation to inhalation (or from inhalation to exhalation) in response. Triggering refers to the transition from exhalation to inhalation in order to distinguish it from the transition from inhalation to exhalation (referred to as cycling). Ventilation systems, depending on their mode of operation, may trigger and/or cycle automatically, or in response to a detection of patient effort, or both.

The ventilatory system 800 may also include one or more distributed sensors 818 communicatively coupled to ventilator 802. Distributed sensors 818 may communicate with various components of ventilator 802, e.g., ventilation module 812, internal sensors 820, data processing module 822, and any other suitable components and/or modules. Distributed sensors 818 may be placed in any suitable location, e.g., within the ventilatory circuitry or other devices communicatively coupled to the ventilator. For example, sensors may be affixed to the ventilatory tubing or may be imbedded in the tubing itself. According to some embodiments, sensors may be provided at or near the lungs (or diaphragm) for detecting a pressure in the lungs, or at some other location on the body (e.g., in the case of Electrical Impedance Tomography, EIT). Additionally or alternatively, sensors may be affixed or imbedded in or near wye-fitting 770 and/or patient interface 780, as described above.

Distributed sensors 818 may further include pressure transducers that may detect changes in circuit pressure (e.g., electromechanical transducers including piezoelectric, variable capacitance, or strain gauge) or changes in a patient's muscular pressure ($P_m$). Distributed sensors 818 may further include various flowmeters for detecting airflow (e.g., differential pressure pneumotachometers). For example, some flowmeters may use obstructions to create a pressure decrease corresponding to the flow across the device (e.g., differential pressure pneumotachometers) and other flowmeters may use turbines such that flow may be determined based on the rate of turbine rotation (e.g., turbine flowmeters). Alternatively, sensors may utilize optical or ultrasound techniques for measuring changes in ventilatory parameters. A patient's blood parameters or concentrations of expired gases may also be monitored by sensors to detect physiological changes that may be used as indicators to study physiological effects of ventilation, wherein the results of such studies may be used for diagnostic or therapeutic purposes. Indeed, any distributed sensory device useful for monitoring changes in measurable parameters during ventilatory treatment may be employed in accordance with embodiments described herein.

Ventilator 802 may further include one or more internal sensors 820. Similar to distributed sensors 818, internal sensors 820 may communicate with various components of ventilator 802, e.g., ventilation module 812, internal sensors 820, data processing module 822, and any other suitable components and/or modules. Internal sensors 220 may employ any suitable sensory or derivative technique for monitoring one or more parameters associated with the ventilation of a patient. However, the one or more internal sensors 820 may be placed in any suitable internal location, such as, within the ventilatory circuitry or within components or modules of ventilator 802. For example, sensors may be coupled to the inhalation and/or exhalation modules for detecting changes in, circuit pressure and/or flow. Specifically, internal sensors may include pressure transducers and flowmeters for measuring changes in circuit pressure and airflow. Additionally or alternatively, internal sensors may utilize optical or ultrasound techniques for measuring changes in ventilatory parameters. For example, the internal sensors may monitor one or more of flow and pressure.

Ventilator 802 may further include a data processing module 822. As noted above, distributed sensors 818 and internal sensors 820 may collect data regarding various ventilatory parameters. A ventilatory parameter refers to any factor, characteristic, or measurement associated with the ventilation of a patient, whether monitored by the ventilator or by any other device. Sensors may further transmit collected data to the data processing module 822 and, according to embodiments, the data processing module 822 may be configured to collect data regarding some ventilatory parameters, to derive data regarding other ventilatory parameters, and/or to graphically represent collected and derived data to the clinician and/or other modules of the ventilatory system. According to embodiments, any collected, derived, and/or graphically represented data may be defined as ventilatory data.

For example, according to embodiments, data processing module 822 may be configured to monitor inspiratory and expiratory flow. Flow may be measured by any appropriate, internal or distributed device or sensor within the ventilatory system. As described above, flowmeters may be employed by the ventilatory system to detect circuit flow. However, any suitable device either known or developed in the future may be used for detecting airflow in the ventilatory circuit.

Data processing module 822 may be further configured to plot monitored flow data graphically via any suitable means. For example, according to embodiments, flow data may be plotted versus time (flow waveform), versus volume (flow-volume loop), or versus any other suitable parameter as may be useful to a clinician. According to embodiments, flow may be plotted such that each breath may be independently identified. Further, flow may be plotted such that inspiratory flow and expiratory flow may be independently identified, e.g., inspiratory flow may be represented in one color and expiratory flow may be represented in another color.

According to embodiments, data processing module 822 may be configured to monitor pressure. Pressure may be measured by any appropriate, internal or distributed device or sensor within the ventilatory system. For example, pressure may be monitored by proximal electromechanical transducers connected near the airway opening (e.g., on the inspiratory limb, expiratory limb, at the patient interface, etc.). Alternatively, pressure may be monitored distally, at or near the lungs and/or diaphragm of the patient.

Data processing module 822 may be further configured to plot monitored pressure data graphically via any suitable means. For example, according to embodiments, pressure data may be plotted versus time (pressure waveform), versus volume (pressure-volume loop or PV loop), or versus any other suitable parameter as may be useful to a clinician. According to embodiments, pressure may be plotted such that each breath may be independently identified. Further, pressure may be plotted such that inspiratory pressure and expiratory pressure may be independently identified, e.g., inspiratory pressure may be represented in one color and expiratory pressure may be represented in another color. According to additional embodiments, pressure waveforms and PV loops, for example, may be represented alongside additional graphical representations, e.g., representations of volume, flow, etc., such that a clinician may substantially simultaneously visualize a variety of parameters associated with each breath.

According to embodiments, data processing module 822 may be configured to derive volume via any suitable means. For example, as described above, during volume ventilation, a prescribed $V_T$ may be set for delivery to the patient. For either volume or pressure ventilation, delivered $V_T$ may be determined at the end of inspiration, i.e., by integrating net inspiratory flow over $T_I$ (either set $T_I$ or patient-determined $T_I$). Alternatively, expiratory flow may be monitored such that exhaled tidal volume ($V_{TE}$) may be derived by integrating net expiratory flow over expiratory time ($T_E$). In general, the delivered $V_T$ should be completely exhaled and, thus, $V_{TE}$ should be equivalent to delivered $V_T$.

Data processing module 822 may be further configured to plot the volume data graphically via any suitable means. For example, according to embodiments, volume data may be plotted versus time (volume waveform), versus flow (flow-volume loop or FV loop), or versus any other suitable parameter as may be useful to a clinician. According to embodiments, volume may be plotted such that each breath may be independently identified. Further, volume may be plotted such that delivered $V_T$ and $V_{TE}$ may be independently identified, e.g., delivered $V_T$ may be represented in one color and $V_{TE}$ may be represented in another color. According to additional embodiments, volume waveforms and FV loops, for example, may be represented alongside additional graphical representations, e.g., representations of pressure, flow, etc., such that a clinician may substantially simultaneously visualize a variety of parameters associated with each breath.

With respect to references made to supplemental text, the following supplemental text may be provided in response to detection of various exemplary anomalies:

Detection of an Anomaly Indicative of Air Trapping (or Auto PEEP):

Auto-PEEP occurs when there is insufficient time for the patient to fully exhale a prescribed volume or pressure. In this case, exhalation time may be set too low. Auto-PEEP may increase a patient's work-of-breathing (WOB). Consider causes such as bronchospasm and dynamic hyperinflation. Consider mitigation such as increasing the PEEP level to bring circuit pressure closer to lung pressure (providing it does not increase lung pressure at the same time) thereby making it easier for an obstructed patient to trigger. If Auto-PEEP is due to dynamic hyperinflation, lung pressure may not increase much with raised PEEP. See link to Tobin, "Waterfall effect." Consider performing an expiratory hold maneuver to determine the Auto-PEEP level, where Auto-PEEP is equal to monitored total PEEP during maneuver minus the set PEEP level.

In some cases, the ventilator may perform one or more of the recommended actions and/or may adjust one or more settings to mitigate the Auto-PEEP. For example, the ventilator may be configured to take prescribed actions in response to specific conditions, e.g., based on advance approval by the clinician. In this case, the ventilator may provide a notification to the clinician of any actions or adjustments.

Detection of Anomaly Indicative of Flow Starvation:

Clinician observes that the patient appears to be pulling too hard, resulting in an increased WOB. The anomaly is recognized by a "lag" in rise rate of the slope of the pressure waveform. This anomaly may be indicative of an inability to deliver necessary flow to meet patient demand (inadequate flow setting). The clinician should be aware that as the flow setting is increased, pressure may also increase. Alternatively, the anomaly may be recognized by failure to attain a plateau pressure in the pressure waveform. This anomaly may also be indicative of a leak of gases from the system.

In some cases, the ventilator may perform one or more of the recommended actions and/or may adjust one or more settings to mitigate flow starvation. For example, the ventilator may be configured to take prescribed actions in response to specific conditions, e.g., based on advance approval by the clinician. In this case, the ventilator may provide a notification to the clinician of any actions or adjustments.

Detection of Anomaly Indicative of Tachypnea:

Tachypnea refers to abnormally rapid breathing. Here, the clinician should be aware of the time scale for the waveform and change scale setting to verify this anomaly. For example, where 17 breaths occur in 48 seconds but only 21 breaths per minute. First, change time scale to a 3-second view to assess the breath and timing. Verify whether patient condition has changed (e.g., change in respiratory rate or patient effort). If tachypneic, first clinically assess patient including external monitoring. Possible causes of tachypnea include a need for suction, patient discomfort, fever, sepsis, unmet respiratory demand, and/or resistance to flow. For unmet respiratory demand, consider an increase in minute ventilation support and flow. For resistance to expiratory flow, consider extending expiratory time, shortening inspiratory time, adjusting PEEP, and/or adjusting trigger sensitivity.

In some cases, the ventilator may perform one or more of the recommended actions and/or may adjust one or more settings to mitigate tachypnea. For example, the ventilator may be configured to take prescribed actions in response to specific conditions, e.g., based on advance approval by the clinician. In this case, the ventilator may provide a notification to the clinician of any actions or adjustments.

Those skilled in the art will recognize that the methods and systems of the present disclosure may be implemented in many manners and as such are not to be limited by the foregoing exemplary aspects and examples. In other words, functional elements being performed by a single or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A ventilator, comprising:
    at least one processor; and
    at least one memory storing computer executable instructions that when executed by the at least one processor cause the ventilator to:
        collect data from one or more sensors monitoring one or more parameters during ventilation of a patient;
        as the data is collected, graphically represent the data as a waveform in a first window of a display operatively coupled to the ventilator;
        monitor at least one of a shape or a characteristic of the waveform;
        detect an anomaly based on at least one of the shape or the characteristic;
        in response to detecting the anomaly, automatically capture a screenshot of the waveform including the anomaly;
        display an anomaly detection icon in the first window;
        receive a selection of the anomaly detection icon; and
        in response to the selection, provide a second window displaying the captured screenshot.

2. The ventilator of claim 1, wherein the waveform is one of flow, pressure, or volume.

3. The ventilator of claim 1, wherein automatically capturing the screenshot of the waveform comprises taking an image of a portion of the waveform.

4. The ventilator of claim 1, wherein automatically capturing the screenshot of the waveform comprises recording a portion of the waveform for a defined length of time.

5. The ventilator of claim 1, wherein the second window displays the captured screenshot with a label of a feature associated with the anomaly on a portion of the waveform associated with the anomaly.

6. The ventilator of claim 1, wherein the second window displays the captured screenshot with one or more of:
    a teaching icon, wherein a selection of the teaching icon displays a teaching graphic including at least one label of a feature of a portion of the waveform associated with the anomaly; or a supplemental inquiry icon, wherein a selection of the supplemental inquiry icon displays supplemental text regarding the anomaly.

7. The ventilator of claim 5, wherein the label indicates a potential issue with the ventilation of the patient based on the anomaly.

8. The ventilator of claim 1, wherein the second window displays supplemental text including one or more of:
- a description of the anomaly;
- one or more potential causes of the anomaly;
- links to scholarly articles regarding the anomaly;
- other patient data collected at the time of anomaly detection in the waveform;
- one or more sample waveforms associated with the anomaly from a population of patients; or
- a suggestion for mitigating a potential issue with the ventilation of the patient associated with the anomaly.

9. The ventilator of claim 1, wherein the second window displays the captured screenshot with an education icon, wherein selection of the education icon displays at least one label of a feature of a portion of the waveform associated with the anomaly and supplemental text regarding the anomaly.

10. The ventilator of claim 3, wherein the second window displays the image of the portion of the waveform.

11. The ventilator of claim 4, wherein the second window plays an animation of the portion of the waveform.

12. The ventilator of claim 1, wherein the second window displays the captured screenshot as an overlay over a second waveform.

13. The ventilator of claim 12, wherein the second waveform is one of:
- a statistically-based waveform associated with the anomaly;
- a patient-specific waveform captured at a different time than the time of anomaly detection; or
- the waveform displayed in the first window.

14. The ventilator of claim 1, the computer executable instructions further causing the ventilator to:
- automatically adjust one or more settings to mitigate a potential issue in ventilation of the patient associated with the anomaly; and
- display a notification regarding the adjustment of the one or more settings.

15. A ventilator-implemented method for providing decision support during ventilation of a patient, comprising:
- collecting, by a ventilator, data from one or more sensors monitoring one or more parameters during ventilation of the patient by a ventilator;
- as the data is collected, graphically representing, by the ventilator, the data as a waveform in a first window of a display operatively coupled to the ventilator;
- monitoring, by the ventilator, at least one of a shape or a characteristic of the waveform;
- detecting, by the ventilator, an anomaly based on at least one of the shape or the characteristic;
- in response to detecting the anomaly, capturing, by the ventilator, a portion of the waveform including the anomaly; and
- providing, by the ventilator, a second window displaying the captured portion of the waveform.

16. The method of claim 15, wherein the second window displays the captured portion of the waveform with a label of a feature associated with the anomaly on the captured portion of the waveform.

17. A ventilator-implemented method for providing decision support during ventilation, comprising:
- collecting, by a ventilator, data from one or more sensors monitoring one or more parameters during ventilation of a patient by a ventilator;
- as the data is collected, graphically representing, by the ventilator, the data as a waveform in a first window of a display operatively coupled to the ventilator;
- monitoring, by the ventilator, at least one of a shape or a characteristic of the waveform;
- detecting, by the ventilator, an anomaly based on at least one of the shape or the characteristic;
- in response to detecting the anomaly, capturing, by the ventilator, a portion of the waveform including the anomaly; and
- displaying, by the ventilator, an anomaly detection icon in the first window.

18. The method of claim 17, further comprising:
- receiving a selection of the anomaly detection icon; and
- in response to the selection, providing a second window displaying the captured portion of the waveform.

19. The method of claim 18, wherein the second window displays the captured portion of the waveform with one or more of:
- a label of a feature associated with the anomaly on the captured portion of the waveform; or
- supplemental text regarding the anomaly.

20. The method of claim 18, wherein capturing the portion of the waveform comprises taking an image of the portion of the waveform.

* * * * *